United States Patent [19]
Yoon

[11] Patent Number: 5,993,466
[45] Date of Patent: *Nov. 30, 1999

[54] SUTURING INSTRUMENT WITH MULTIPLE ROTATABLY MOUNTED SPREADABLE NEEDLE HOLDERS

[76] Inventor: InBae Yoon, 2101 Highland Ridge Dr., Phoenix, Md. 21131

[*] Notice: This patent issued on a continued prosecution application filed under 37 CFR 1.53(d), and is subject to the twenty year patent term provisions of 35 U.S.C. 154(a)(2).

[21] Appl. No.: 08/877,764

[22] Filed: Jun. 17, 1997

[51] Int. Cl.⁶ .................................................. A61B 17/04
[52] U.S. Cl. ......................... 606/147; 606/144; 606/148
[58] Field of Search .................................. 606/144, 145, 606/147, 148, 139, 205, 206

[56] References Cited

U.S. PATENT DOCUMENTS

| | | |
|---|---|---|
| 919,138 | 4/1909 | Drake et al. . |
| 1,037,864 | 9/1912 | Carlson et al. . |
| 1,131,163 | 3/1915 | Saunders et al. . |
| 1,155,378 | 10/1915 | Steedman . |
| 1,449,087 | 3/1923 | Bugbee . |
| 1,822,330 | 9/1931 | Ainslie . |
| 1,916,722 | 7/1933 | Ende . |
| 2,213,830 | 9/1940 | Anastasi . |
| 2,580,964 | 1/1952 | Skaller . |
| 2,601,564 | 6/1952 | Smith . |
| 2,646,045 | 7/1953 | Priestley . |
| 2,959,172 | 11/1960 | Held . |
| 3,090,386 | 5/1963 | Curtis . |
| 3,139,089 | 6/1964 | Schwerin . |
| 3,349,772 | 10/1967 | Rygg . |
| 3,470,875 | 10/1969 | Johnson . |
| 3,842,840 | 10/1974 | Schweizer . |
| 3,946,740 | 3/1976 | Bassett . |
| 4,109,658 | 8/1978 | Hughes . |
| 4,164,225 | 8/1979 | Johnson et al. . |
| 4,257,420 | 3/1981 | Terayama . |
| 4,440,171 | 4/1984 | Nomoto et al. . |
| 4,557,265 | 12/1985 | Andersson . |
| 4,621,640 | 11/1986 | Mulhollan et al. . |

(List continued on next page.)

FOREIGN PATENT DOCUMENTS

| | | |
|---|---|---|
| 0482881A1 | 4/1992 | European Pat. Off. . |
| 0337579 | 4/1904 | France . |
| 0395073 | 8/1973 | U.S.S.R. . |
| 2260704 | 9/1991 | United Kingdom . |
| WO 97/37583 | 10/1997 | WIPO . |

*Primary Examiner*—Michael Powell Buiz
*Assistant Examiner*—Julian W. Woo
*Attorney, Agent, or Firm*—Blank Rome Comisky & McCauley LLP

[57] ABSTRACT

An instrument for suturing anatomical tissue with a suture needle includes a housing, an elongate shaft having a proximal end mounted by the housing and a distal end with a peripheral edge, a first needle holder protruding from the distal end of the elongate shaft and having a needle holding member at a distal end operable to grasp and release a suture needle, and a second needle holder protruding from the distal end of the elongate shaft and having a needle holding member at a distal end operable to grasp and release a suture needle. Distal portions of the first and second needle holders extend laterally outward at an angle from first and second longitudinal axes of the elongate shaft to positions where at least a portion of the corresponding needle holding members are spaced laterally outward of the peripheral edge of the elongate shaft. In addition, the needle holders are rotatable about the first and second longitudinal axes of the elongate shaft to cause the corresponding needle holding members to move along first and second arcuate paths. When inserting the suturing instrument through a portal in an endoscopic procedure, the first and second needle holders are preferably movable to undeployed positions where their needle holding members are spaced laterally inward of the peripheral edge of the elongate shaft. When suturing, the needle holding members can be moved from their undeployed positions to deployed positions disposed laterally outward of the peripheral edge due to the angled configuration of the distal portions of the needle holders.

60 Claims, 10 Drawing Sheets

U.S. PATENT DOCUMENTS

| | | |
|---|---|---|
| 4,635,638 | 1/1987 | Weintraub et al. . |
| 4,935,027 | 6/1990 | Yoon . |
| 5,037,433 | 8/1991 | Wilk et al. . |
| 5,100,421 | 3/1992 | Christoudias . |
| 5,147,373 | 9/1992 | Ferzli . |
| 5,152,769 | 10/1992 | Baber . |
| 5,171,257 | 12/1992 | Ferzli . |
| 5,181,919 | 1/1993 | Bergman et al. . |
| 5,209,741 | 5/1993 | Spaeth . |
| 5,211,650 | 5/1993 | Noda . |
| 5,222,508 | 6/1993 | Contarini . |
| 5,224,948 | 7/1993 | Abe et al. . |
| 5,234,443 | 8/1993 | Phan et al. . |
| 5,244,948 | 9/1993 | Mulhaupt et al. . |
| 5,261,917 | 11/1993 | Hasson et al. . |
| 5,281,238 | 1/1994 | Chin et al. . |
| 5,300,082 | 4/1994 | Sharpe et al. . |
| 5,304,185 | 4/1994 | Taylor . |
| 5,305,121 | 4/1994 | Moll . |
| 5,308,353 | 5/1994 | Beurrier . |
| 5,320,632 | 6/1994 | Heidmueller . |
| 5,336,230 | 8/1994 | Leichtling et al. . |
| 5,336,231 | 8/1994 | Adair . |
| 5,356,424 | 10/1994 | Buzerak et al. . |
| 5,364,408 | 11/1994 | Gordon . |
| 5,364,409 | 11/1994 | Kuwabara et al. . |
| 5,374,275 | 12/1994 | Bradley et al. . |
| 5,376,096 | 12/1994 | Foster . |
| 5,389,098 | 2/1995 | Tsuruta et al. . |
| 5,389,103 | 2/1995 | Melzer et al. . |
| 5,395,367 | 3/1995 | Wilk . |
| 5,397,325 | 3/1995 | Della Badia et al. . |
| 5,403,328 | 4/1995 | Shallman . |
| 5,403,329 | 4/1995 | Hinchcliffe . |
| 5,437,681 | 8/1995 | Meade et al. . |
| 5,454,823 | 10/1995 | Richardson et al. . |
| 5,462,561 | 10/1995 | Voda . |
| 5,462,562 | 10/1995 | Elkus . |
| 5,468,251 | 11/1995 | Buelna . |
| 5,470,338 | 11/1995 | Whitfield et al. . |
| 5,474,057 | 12/1995 | Makower et al. . |
| 5,474,568 | 12/1995 | Scott . |
| 5,477,794 | 12/1995 | Klundt . |
| 5,478,344 | 12/1995 | Stone et al. . |
| 5,478,345 | 12/1995 | Stone et al. . |
| 5,480,406 | 1/1996 | Nolan et al. . |
| 5,496,310 | 3/1996 | Exconde et al. . |
| 5,496,334 | 3/1996 | Klundt et al. . |
| 5,503,634 | 4/1996 | Christy . |
| 5,520,703 | 5/1996 | Essig et al. . |
| 5,540,704 | 7/1996 | Gordon et al. . |
| 5,540,705 | 7/1996 | Meade et al. . |
| 5,545,148 | 8/1996 | Wurster . |
| 5,562,640 | 10/1996 | McCabe et al. . |
| 5,562,685 | 10/1996 | Mollenauer et al. . |
| 5,562,686 | 10/1996 | Sauer et al. . |
| 5,562,703 | 10/1996 | Desai . |
| 5,569,164 | 10/1996 | Lurz . |
| 5,569,269 | 10/1996 | Hart et al. . |
| 5,569,270 | 10/1996 | Weng . |
| 5,573,542 | 11/1996 | Stevens . |
| 5,578,048 | 11/1996 | Pasqualucci et al. . |
| 5,582,617 | 12/1996 | Klieman et al. . |
| 5,591,181 | 1/1997 | Stone et al. . |
| 5,601,575 | 2/1997 | Measamer et al. . |
| 5,603,718 | 2/1997 | Xu . |
| 5,607,435 | 3/1997 | Sachdeva et al. . |
| 5,609,601 | 3/1997 | Kolesa et al. . |
| 5,626,588 | 5/1997 | Sauer et al. . |
| 5,632,751 | 5/1997 | Piraka . |
| 5,632,752 | 5/1997 | Buelna . |
| 5,643,292 | 7/1997 | Hart . |
| 5,662,663 | 9/1997 | Shallman . |
| 5,674,230 | 10/1997 | Tovey et al. . |
| 5,702,407 | 12/1997 | Kaji . |
| 5,707,379 | 1/1998 | Fleenor et al. . |
| 5,709,693 | 1/1998 | Taylor . |
| 5,709,694 | 1/1998 | Greenberg et al. . |
| 5,713,908 | 2/1998 | Jameel et al. . |
| 5,722,990 | 3/1998 | Sugarbaker et al. . |
| 5,741,277 | 4/1998 | Gordon et al. ................ 606/147 |
| 5,810,805 | 9/1998 | Sutcu et al. . |

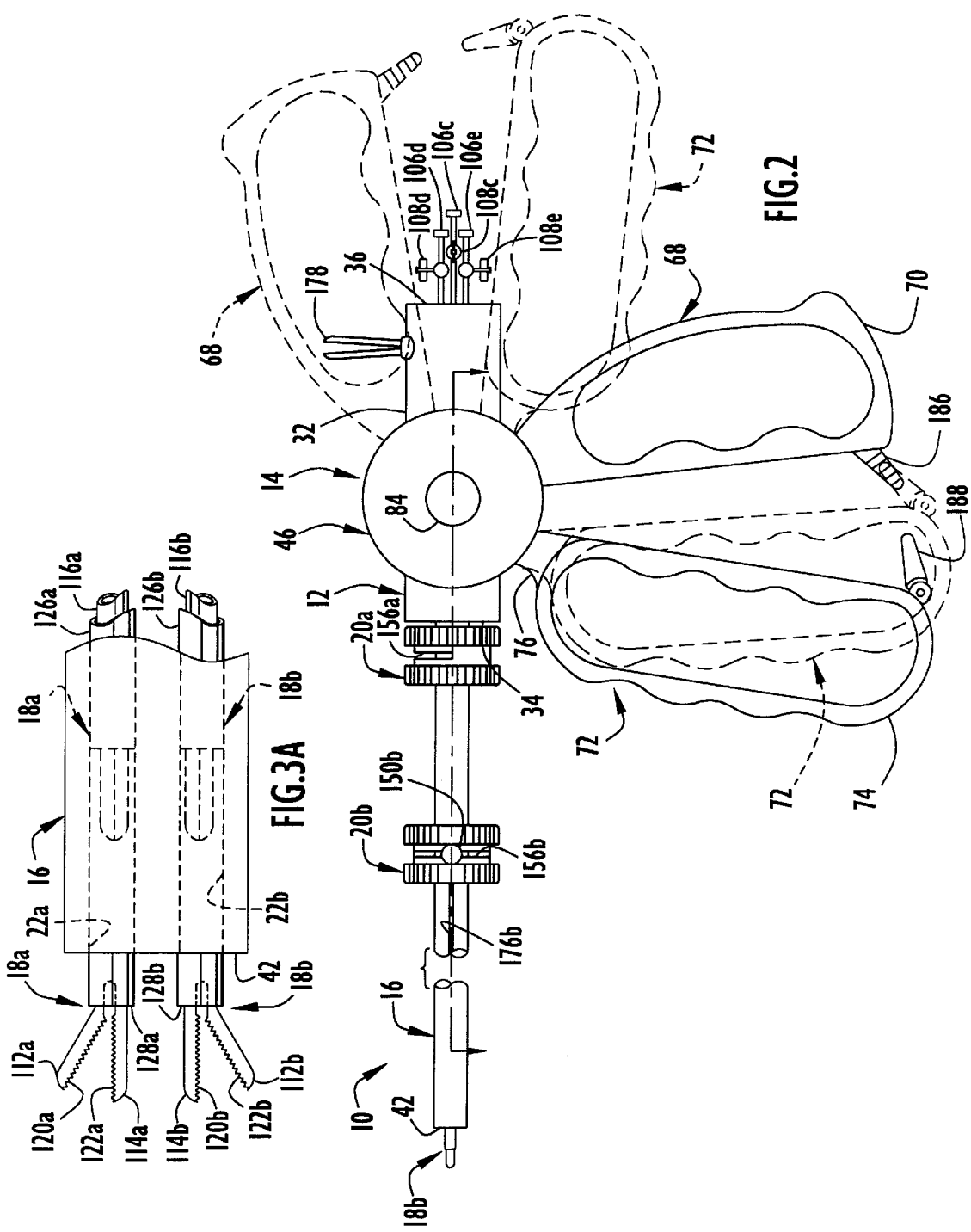

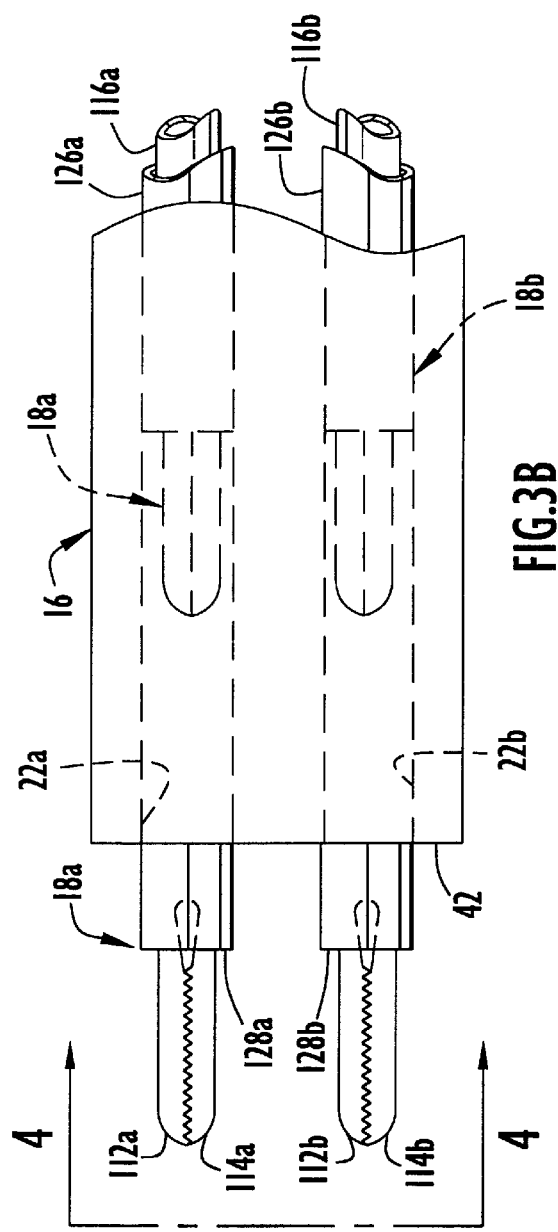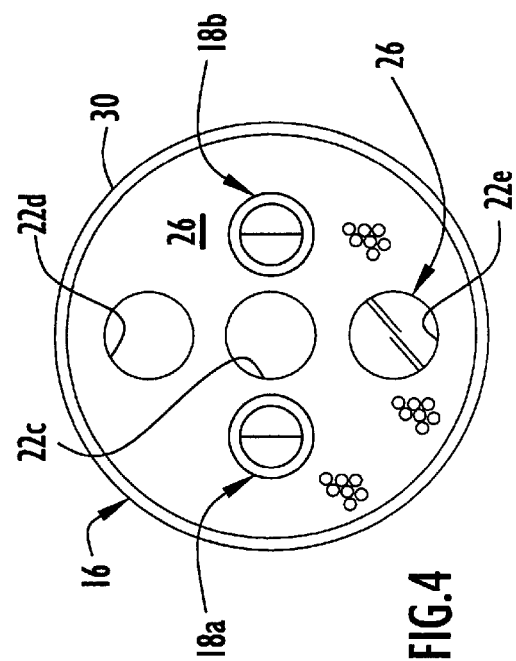

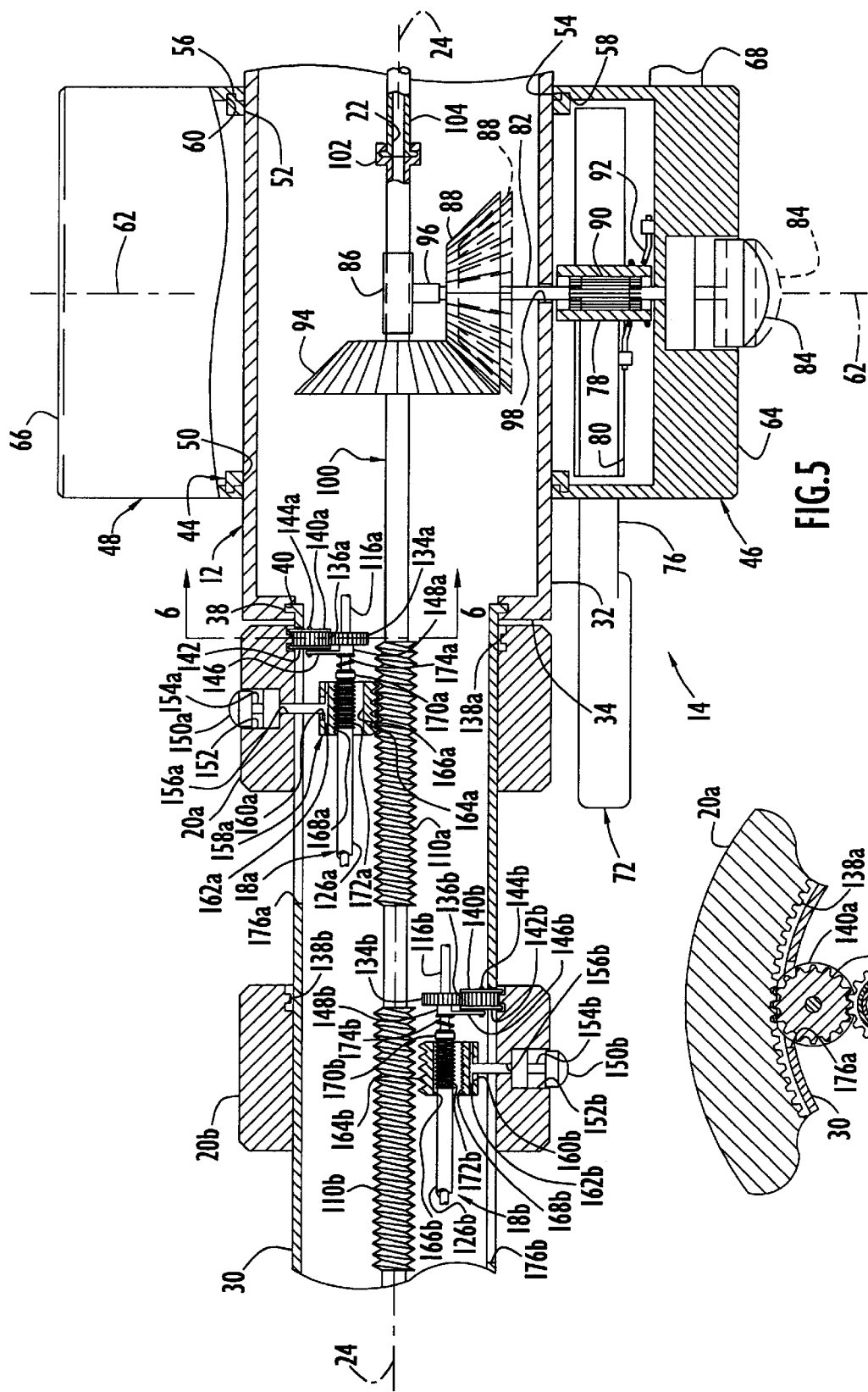

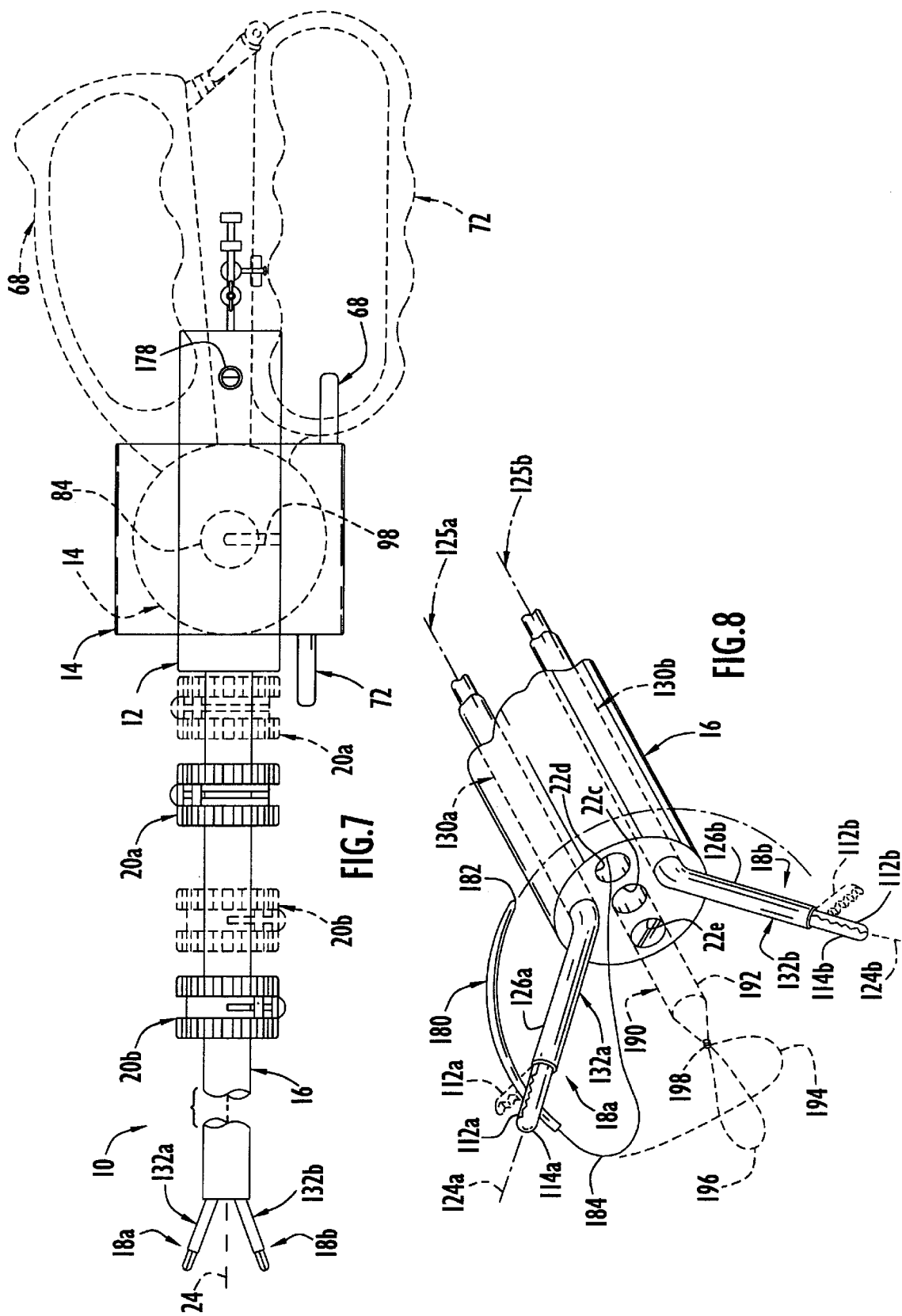

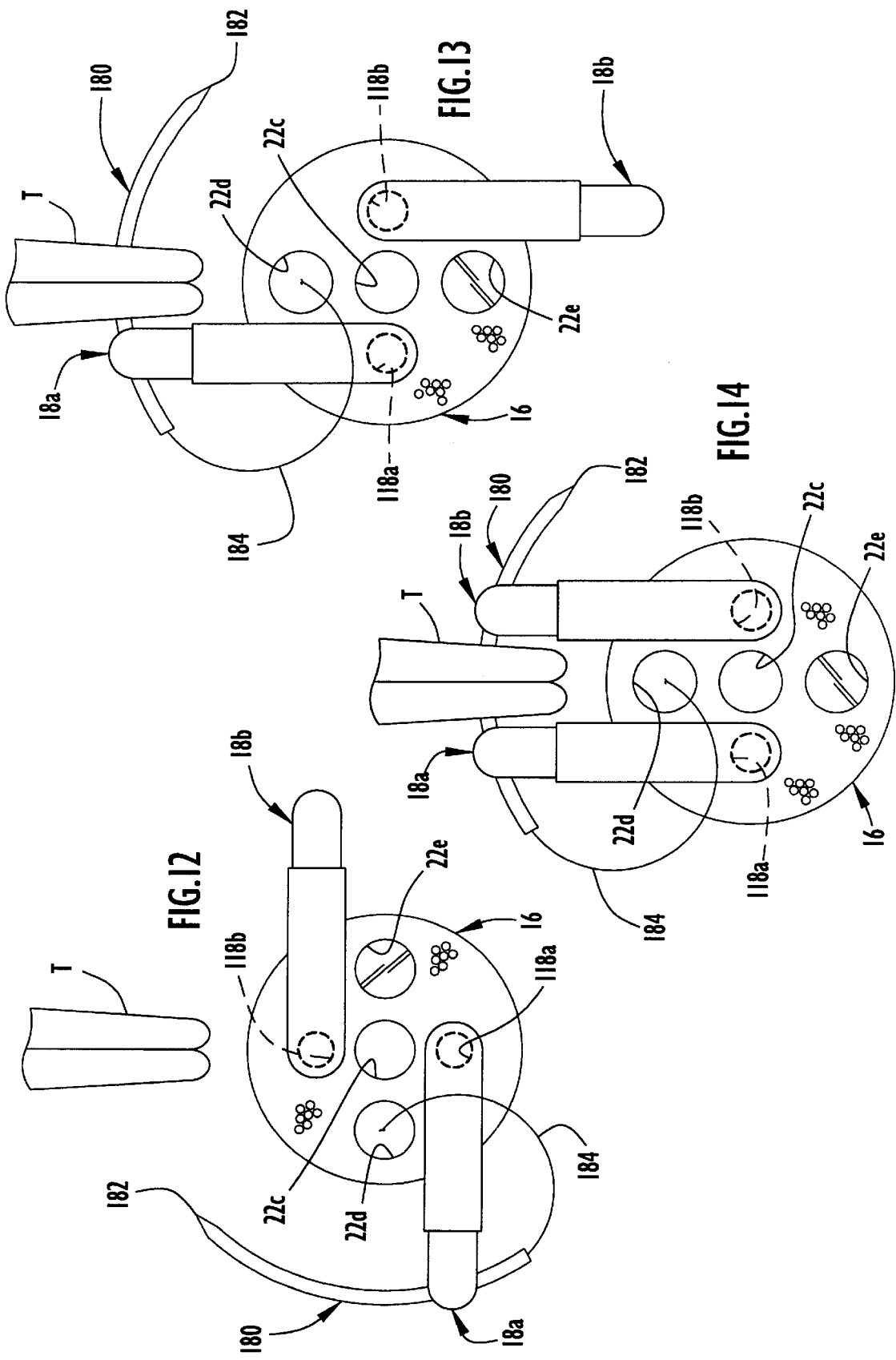

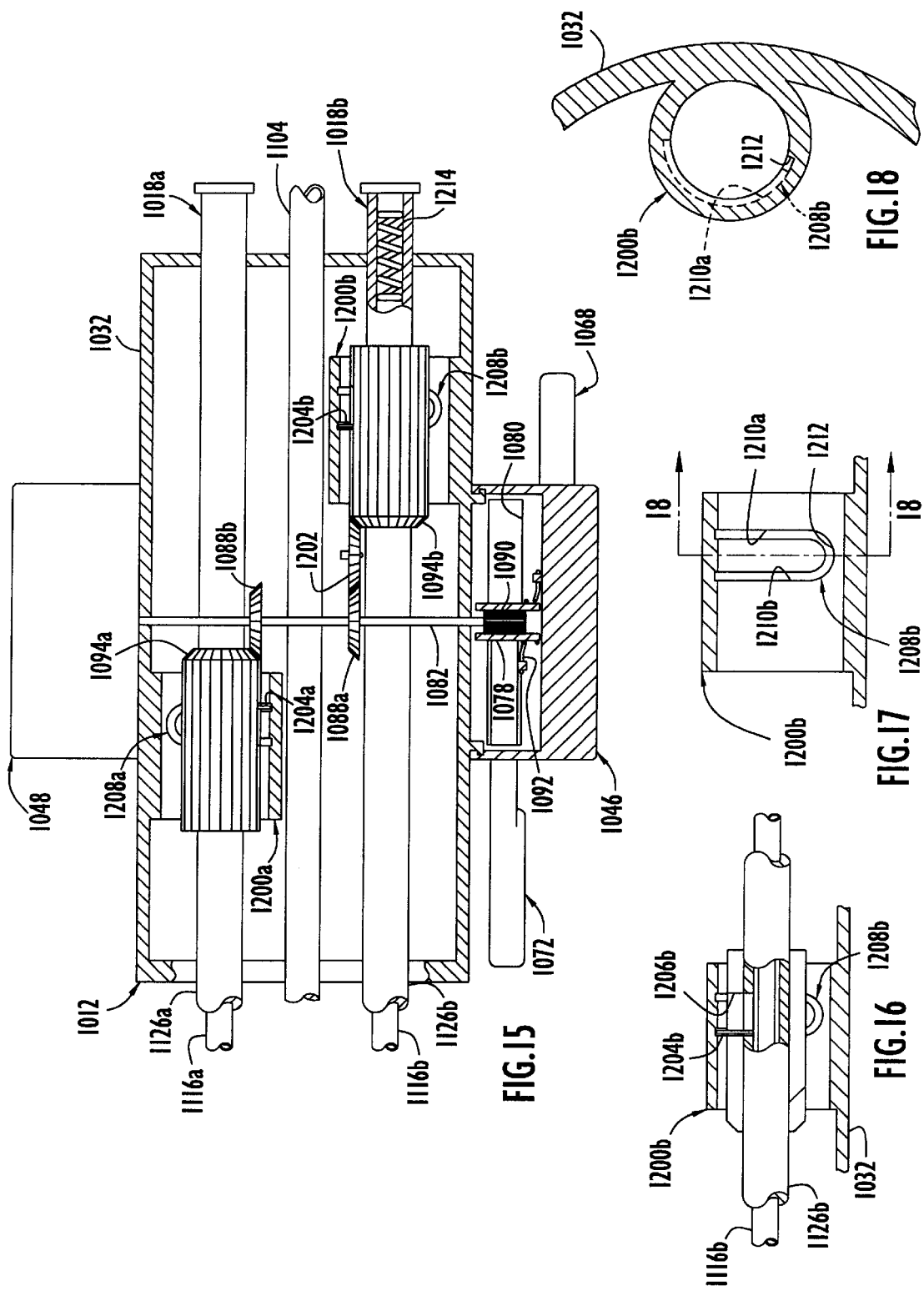

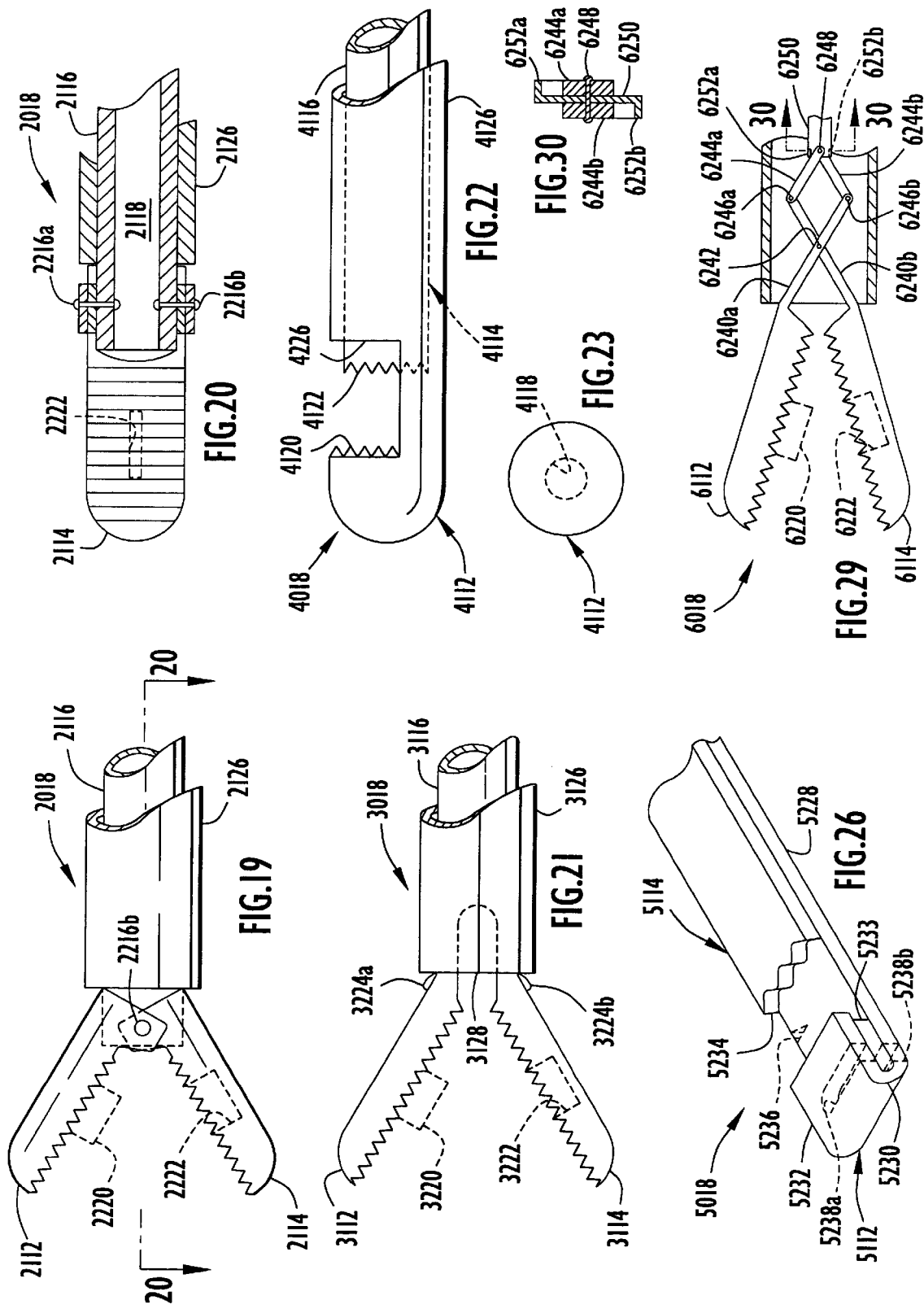

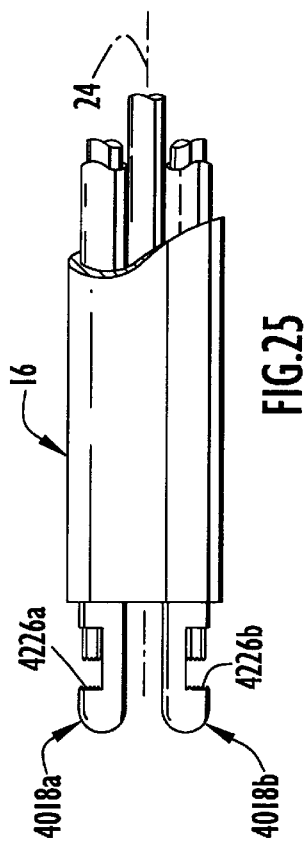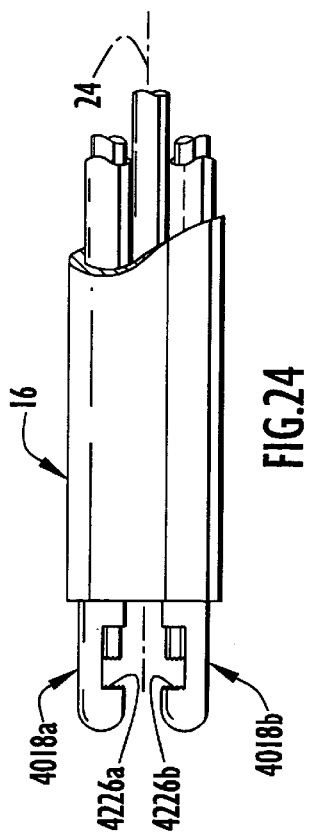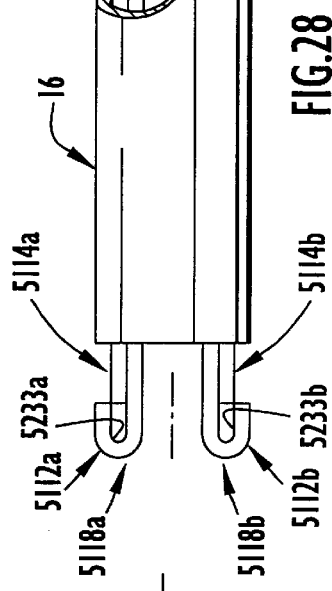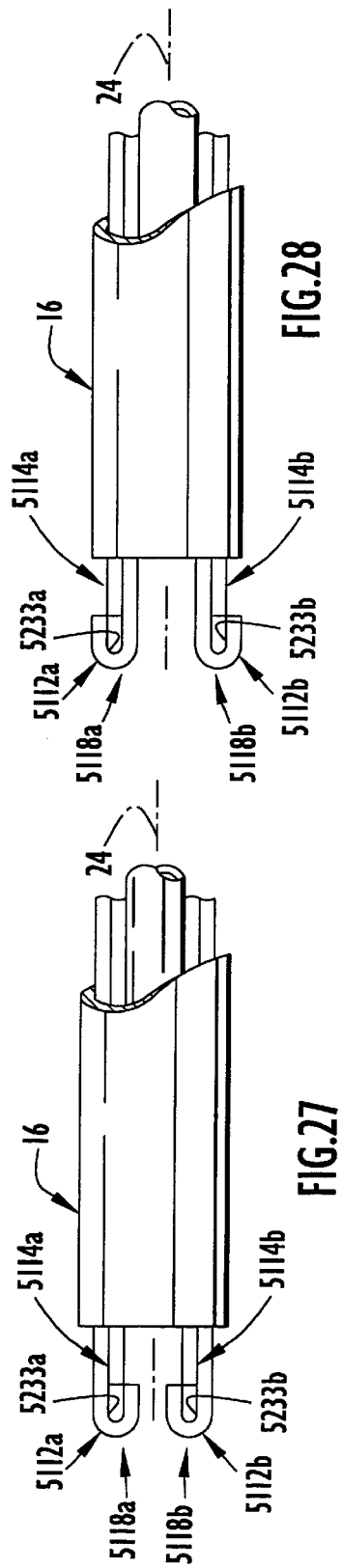

SUTURING INSTRUMENT WITH MULTIPLE ROTATABLY MOUNTED SPREADABLE NEEDLE HOLDERS

BACKGROUND OF THE INVENTION

1. Field of the Invention

The present invention pertains to suturing of bodily or anatomical tissue and, more particularly, to an apparatus and method for suturing anatomical tissue during endoscopic and open surgical procedures.

2. Discussion of the Related Art

Suturing of bodily tissue, that is, the practice of using lengths of suture material to ligate or approximate tissue, is a time consuming part of most surgical procedures including both open surgery and endoscopic or closed surgery. By "open surgery" is meant surgery wherein the surgeon gains access to the surgical site by a relatively large incision and by "endoscopic surgery" is meant minimally invasive surgery wherein the surgeon gains access to the surgical site via one or more portals through which endoscopes are introduced to view the surgical site and through which instruments, such as forceps, cutters, needle holders and the like, are introduced to the surgical site.

In the past, suturing has been accomplished with the use of a sharp suture needle carrying a length of suture material, the suture needle being caused to penetrate and pass through the tissue pulling the suture material through the tissue. Once the suture material has been pulled through the tissue, the surgeon ties a knot in the suture material, the knotting procedure allowing the surgeon to adjust the tension on the suture material to accommodate the particular tissue being sutured and to control approximation, occlusion, attachment or other conditions of the tissue.

The process of tissue penetration and knotting of the suture material can be time consuming and tedious work, particularly when performed in connection with microsurgery and endoscopic surgery and can unduly prolong the duration of surgery and therefore the period during which the patient is under anesthesia. Nevertheless, endoscopic surgery is preferred over open surgery due to the greatly reduced trauma and wound healing time for the patient and due to cost savings associated with shorter hospital stays and performing surgery in non-hospital or out-patient surgery sites. Accordingly, there has been much effort to develop techniques for facilitating the suturing normally performed by use of a suture needle and a length of suture material. Alternative techniques proposed have included electrical coagulation, mechanical devices such as clips, clamps and staples, and lasers; however, no alternative technique has yet been well accepted by surgeons to produce the results obtained by suturing and tying. Thus, there is a great need for suturing techniques useful in endoscopic surgery to permit surgeons to suture anatomical tissue using suture needles and lengths of suture material in a time efficient, consistent and precise manner.

The performance of an endoscopic procedure typically involves creation of one or a number of puncture sites through a wall of an anatomical cavity using a penetrating instrument including an obturator, such as a trocar, disposed within a portal sleeve. After the penetrating instrument has penetrated into the anatomical cavity, the obturator is withdrawn leaving the sleeve in place to form a portal in the cavity wall for the introduction of instruments such as endoscopes, scissors, forceps, needle holders and the like into the anatomical cavity. Suturing is typically performed with a needle holding instrument or needle holder having a pair of jaws adapted to hold the body of a suture needle. The jaws of the needle holding instrument are inserted through the portal sleeve and are positioned at the operative site by manipulation of a handle at the proximal end of the instrument outside the body. With a suture needle held between the jaws of the needle holding instrument, the handle is manipulated to cause a tip of the needle to be pushed through the tissue being sutured. Once the tip of the suture needle has been pushed through the tissue, the jaws of the needle holding instrument must either be opened to release the suture needle so that the tip of the needle can be grasped and pulled through the tissue therewith, or a second needle holding instrument must be introduced at the operative site through another portal to grasp the tip of the suture needle after it has emerged from the tissue being sutured. The former technique requires further adjustment of the suture needle within the jaws of the needle holder before another stitch can be made; and, while use of a second needle holding instrument for pulling the needle through the anatomical tissue allows the first needle holding instrument to grasp the body of the suture needle in the manner required to make additional stitches, it is generally desirable to minimize the number of puncture sites created for performing a particular endoscopic procedure.

SUMMARY OF THE INVENTION

Accordingly, it is a primary object of the present invention to overcome the above-mentioned disadvantages of the prior art and to improve suturing instruments and methods of suturing anatomical tissue.

Another object of the present invention is to permit suturing of anatomical tissue without the need of having to use multiple needle holding instruments.

Yet another object of the present invention is to minimize the number of puncture sites required for suturing anatomical tissue in an endoscopic procedure by inserting a pair of needle holders through a single portal with a suturing instrument that is operable to move the needle holders relative to one another in a cooperative manner to suture anatomical tissue.

It is a further object of the present invention to permit a suturing instrument as well as other medical instruments and devices to be introduced through a single portal in an endoscopic procedure without the need of having to withdraw the suturing instrument from the portal.

An additional object of the present invention is to increase the range of relative movement or working span of a pair of needle holders inserted through a single portal with a suturing instrument in an endoscopic procedure without the need of having to increase the size of the portal.

Some of the advantages of the present invention over the prior art are that suturing of anatomical tissue in an endoscopic procedure can be accomplished using standard suture needles and filamentous suture materials in a time efficient, consistent and precise manner, that relatively long suture needles can be used to suture thick tissue without the need of having to insert additional instruments at the operative site, that single-handed suturing is made possible, that conventional handle structures can be used to provide users with a familiar feel and to decrease adaptation time, and that the instrument can be made sterilizable for reuse or disposable for single patient use as desired.

The present invention is generally characterized in an instrument for suturing anatomical tissue with a suture needle including a housing, an elongate shaft having a proximal end mounted by the housing and a distal end with a peripheral edge, a first needle holder protruding from the distal end of the elongate shaft and having a needle holding member at a distal end operable to grasp and release a suture needle, and a second needle holder protruding from the distal end of the elongate shaft and having a needle holding member at a distal end operable to grasp and release a suture needle. A distal portion of the first needle holder extends laterally outward at an angle from a first longitudinal axis of the elongate shaft to a position where at least a portion of the corresponding needle holding member is spaced laterally outward of the peripheral edge of the elongate shaft. In addition, the first needle holder is rotatable about the first longitudinal axis of the elongate shaft to cause the corresponding needle holding member to move along a first arcuate path having a center of curvature coaxial with the first longitudinal axis. In a preferred embodiment, a distal portion of the second needle holder extends laterally outward at an angle from a second longitudinal axis of the elongate shaft to a position where at least a portion of the corresponding needle holding member is spaced laterally outward of the peripheral edge of the shaft. The second needle holder can also be mounted for rotation about the second longitudinal axis in order to cause the corresponding needle holding member to move along a second arcuate path having a center of curvature coaxial with the second longitudinal axis. When inserting the suturing instrument through a portal in an endoscopic procedure, the first and second needle holders are preferably movable to undeployed positions where their needle holding members are spaced laterally inward of the peripheral edge of the elongate shaft. When suturing, however, the needle holding members can be moved from their undeployed positions to deployed positions disposed laterally outward of the peripheral edge due to the angled configuration of the distal portions of the needle holders.

In one embodiment, the first and second needle holders are moved between their undeployed, insertion positions and their deployed, working positions via axial movement relative to the elongate shaft. Either needle holder can be used to drive a suture needle through anatomical tissue or to catch a suture needle so that it can be pulled completely through the tissue. The driving and catching functions can be accomplished by rotating the appropriate needle holder relative to the elongate shaft or rotating the appropriate needle holder with the elongate shaft as a unit, dependent upon the procedure to be performed in the preference of the user. One or more operating channels are preferably defined through the elongate shaft to provide access to the operative site from outside the body.

An additional aspect of the present invention is generally characterized in a instrument for suturing anatomical tissue with a suture needle including a housing, an elongate shaft having a proximal end mounted by the housing and a distal end with a peripheral edge, and first and second needle holders protruding from the distal end of the shaft. The first needle holder has a proximal portion extending at least part way through the elongate shaft along a first longitudinal axis, a distal portion extending laterally outward from the proximal portion at an angle, and a needle holding member mounted on the distal portion and operable to grasp and release a suture needle, the proximal portion of the first needle holder being rotatably mounted within the elongate shaft to move the needle holding member of the first needle holder along a first arcuate path having a center of curvature coaxial with the first longitudinal axis. Similarly, the second needle holder has a proximal portion extending at least part way through the elongate shaft along a second longitudinal axis laterally spaced from the first longitudinal axis, a distal portion extending laterally outward from the proximal portion at an angle, and a needle holding member mounted on the distal portion and operable to grasp and release a suture needle, the proximal portion of the second needle holder being rotatably mounted within the elongate shaft to move the needle holding member of the second needle holder along a second arcuate path having a center of curvature coaxial with said second longitudinal axis. Preferably, the first arcuate path has a radius of curvature causing at least a portion of the needle holding member of the first needle holder to extend outwardly of the peripheral edge of the elongate shaft and the second arcuate path has a radius of curvature causing at least a portion of the needle holding member of the second needle holder to extend outwardly of the peripheral edge of the elongate shaft.

Another aspect of the present invention is generally characterized in a method of suturing anatomical tissue using a length of suture material attached to a suture needle, the method including the steps of grasping the suture needle with a needle driver protruding distally from the distal end of an elongate shaft, the needle driver including a distal portion extending laterally outward at an angle from a first longitudinal axis of the elongate shaft, positioning the anatomical tissue between a tip of the suture needle and a needle catcher protruding distally from the distal end of the elongate shaft, the needle catcher including a distal portion extending laterally outward at an angle from a second longitudinal axis of the elongate shaft, rotating the needle driver about the first longitudinal axis to drive the suture needle through the anatomical tissue in a first direction along a first arcuate path coaxial with the first longitudinal axis, receiving the tip of the suture needle in the needle catcher, grasping the suture needle with the needle catcher, releasing the suture needle from the needle driver, and using the needle catcher to pull the suture needle through the anatomical tissue in the first direction along a second arcuate path. The step of using the needle catcher preferably includes the step of rotating the needle catcher about the second longitudinal axis of the elongate shaft to pull the suture needle through the anatomical tissue in the first direction along a second arcuate path coaxial with the second longitudinal axis. After the suture needle has been released from the needle driver, the needle driver can be rotated in a second direction opposite the first direction to receive the tip of the suture needle held by the needle catcher, after which the suture needle is grasped by the needle driver, released from the needle catcher, and the needle driver rotated in the first direction to cause the tip of the suture needle to penetrate through the anatomical tissue a second time.

Still another aspect of the present invention is generally characterized in a method of suturing anatomical tissue using a length of suture material attached to a suture needle, the method including the steps of grasping the suture needle with a needle driver protruding distally from a distal end of an elongate shaft, the needle driver including a distal portion extending laterally outward at an angle from a first longitudinal axis of the elongate shaft, positioning the anatomical tissue between a tip of the suture needle and a needle catcher protruding distally from the distal end of the elongate shaft, the needle catcher including a distal portion extending laterally outward at an angle from a second longitudinal axis of the elongate shaft, using the needle driver to drive the suture needle through the anatomical tissue in a first direction along a first arcuate path coaxial with the first longitudinal axis, receiving the tip of the suture needle and the needle catcher, grasping the suture needle with the needle catcher, releasing the suture needle from the needle driver, and rotating the needle catcher about the second longitudinal axis to pull the suture needle through the anatomical tissue in the first direction along a second arcuate path. In one embodiment, the step of using the needle driver includes rotating the elongate shaft with the needle driver as a unit about the longitudinal axis of the elongate shaft to drive the suture needle through the anatomical tissue. Alternatively, the needle driver can be rotated about the first longitudinal axis of the shaft to drive the suture needle through the anatomical tissue without the need of having to move the shaft.

Other objects and advantages of the present invention will become apparent from the following description of the preferred embodiments taken in conjunction with the accompanying drawings, wherein like parts in each of the several figures are identified by the same reference numerals or by reference numerals having the same last three digits.

BRIEF DESCRIPTION OF THE DRAWINGS

FIG. 2 is a side view, broken longitudinally, of the suturing instrument shown in FIG. 1.

FIG. 3A is a fragmentary top view of the distal end of the suturing instrument shown in FIG. 2 with a pair of needle holders in axially retracted, open positions.

FIG. 3B is a fragmentary top view of the distal end of the suturing instrument shown in FIG. 2 with the needle holders in axially retracted, closed positions.

FIG. 4 is an enlarged front view of the distal end of the suturing instrument taken along line 4—4 in FIG. 3B.

FIG. 5 is a fragmentary top view, partly in section, taken through line 5—5 in FIG. 2.

FIG. 6 is a fragmentary cross-sectional view of a needle holder rotating mechanism for use with the suturing instrument according to the present invention taken through line 6—6 in FIG. 5.

FIG. 7 is a top view, broken longitudinally, of the suturing instrument according to the present invention with the needle holders in axially extended, deployed positions.

FIG. 8 is a fragmentary perspective view of the distal end of the suturing instrument shown in FIG. 7.

FIGS. 12–14 are front views of a suturing instrument illustrating another method of suturing anatomical tissue according to the present invention.

FIG. 15 is a fragmentary top view, partly in section, illustrating a modified operating mechanism for use with the suturing instrument according to the present invention.

FIG. 16 is an enlarged fragmentary view of a portion of the operating mechanism shown in FIG. 15.

FIG. 17 is a fragmentary cross-sectional view of the guide member shown in FIG. 16.

FIG. 18 is a cross-sectional view of the guide member taken through line 18—18 in FIG. 17.

FIG. 19 is a fragmentary side view of a modified needle holder for use with the suturing instrument according to the present invention.

FIG. 20 is a cross-sectional view of the modified needle holder of FIG. 19 taken through line 20—20.

FIG. 21 is a fragmentary side view of another modification of a needle holder for use with the suturing instrument according to the present invention.

FIGS. 22 and 23 are a fragmentary side view and a front view, respectively, of yet another modified needle holder for use with the suturing instrument according to the present invention.

FIG. 24 is a fragmentary side view of the distal end of a suturing instrument according to the present invention with a pair of modified needle holders as shown in FIG. 22 oriented to face inwardly.

FIG. 25 is a fragmentary side view of the distal end of a suturing instrument according to the present invention with a pair of modified needle holders as shown in FIG. 22 oriented to face outwardly.

FIG. 26 is a fragmentary perspective view of still another modification of a needle holder for use with a suturing instrument according to the present invention.

FIG. 27 is a fragmentary side view of the distal end of a suturing instrument according to the present invention with a pair of modified needle holders as shown in FIG. 26 oriented to face inwardly.

FIG. 28 is a fragmentary side view of the distal end of a suturing instrument according to the present invention with a pair of modified needle holders as shown in FIG. 26 oriented to face outwardly.

FIG. 29 is a fragmentary side view, partly in section, of yet another modification of a needle holder for use with a suturing instrument according to the present invention.

FIG. 30 is a cross-sectional view of the needle holder shown in FIG. 29 taken through line 30—30.

DETAILED DESCRIPTION OF THE PREFERRED EMBODIMENTS

Figure 1:
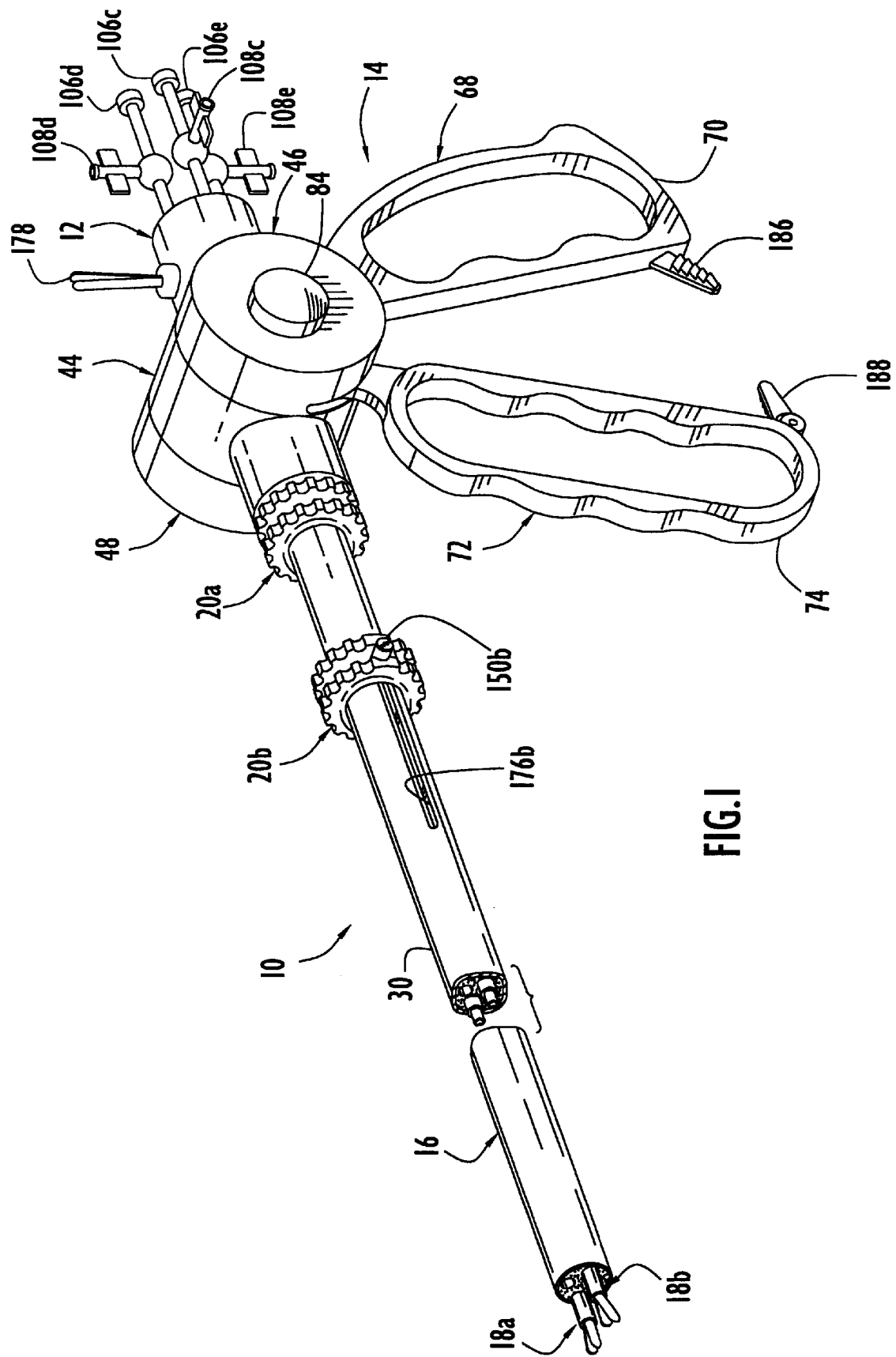
FIG. 1 is a perspective view, broken longitudinally, of a suturing instrument according to the present invention.

The suturing instrument of the present invention can be utilized to suture any type of anatomical tissue in any type of anatomical cavity; and, accordingly, while the instrument is described hereinafter for use with a portal sleeve in endoscopic procedures, such as laparoscopy, the instrument can be used in open surgery and with catheters and other small and large diameter tubular or hollow, cylindrical members providing access to small cavities, such as veins and arteries, as well as large cavities, such as the abdomen.

A suturing instrument 10 in accordance with the present invention, as illustrated in FIGS. 1–6, includes a hub or housing 12, a handle 14 coupled with the housing, an elongate shaft or barrel 16 extending distally from the housing, a pair of needle holders 18a and 18b movably disposed within longitudinal channels formed through the shaft, and a pair of collars 20a and 20b disposed distally of the housing at axially spaced locations along the length of the shaft to control operation of the needle holders in conjunction with the handle.

As best seen in FIG. 4, elongate shaft 16 is of generally cylindrical configuration with a plurality of longitudinally extending passages or channels 22a, 22b, 22c, 22d and 22e defined therethrough in spaced, parallel relation, the channels each being of generally circular configuration in transverse cross-section. Channel 22c is disposed coaxial with a central longitudinal axis 24 of the shaft. Channels 22a and 22b are laterally offset from central channel 22c and are disposed on opposite sides of the central channel in diametrically opposed relation. Channels 22d and 22e are laterally offset from central channel 22c and are defined in the spaces between channels 22a and 22b. Needle holders 18a and 18b are shown extending through channels 22a and 22b, respectively, and an endoscope 26 of conventional design is shown extending through channel 22e. Channels 22c and 22d are shown in an open condition to provide access to an anatomical body cavity from outside the body via the suturing instrument without the need of having to create additional incisions or punctures through the wall of the anatomical cavity. Optical fibers 28 are shown extending through shaft 16 to transmit light from a proximal light source to the body cavity of the patient. The optical fibers are shown extending through a tubular member or sleeve 30 forming the outer surface of the shaft, however, the shaft can be formed without a separate sleeve, for example by embedding or molding the optical fibers within a medically acceptable polymer matrix or by adhesively connecting the fibers together. Channels 22a, 22b, 22c, 22d and 22e can optionally be formed by thin wall, tubular sleeves extending longitudinally through shaft 16 or by voids or spaces defined between the optical fibers as shown.

As best seen in FIGS. 2 and 5, housing 12 includes a hollow, cylindrical portion or side wall 32 with longitudinally spaced front and rear walls 34 and 36 oriented perpendicular to longitudinal axis 24 of the shaft. Tubular member 30 of the shaft extends distally from an outwardly extending flange 38 fixedly mounted within a recess 40 formed in the front wall of housing 12 to a distal end of generally blunt configuration which cooperates with respective distal ends of the optical fibers to define a generally flat surface or face 42 at a distal end of the shaft, the distal face being shown oriented substantially perpendicular to the longitudinal axis of the shaft for purposes of illustration.

Handle 14 includes a central portion 44 of generally cylindrical configuration oriented perpendicular to the longitudinal axis of shaft 16 and a pair of end caps or end portions 46 and 48 of generally cylindrical configuration disposed at opposite axial ends of the cylindrical central handle portion. Central handle portion 44 is of larger diameter than housing 12 and is provided with axially aligned openings or holes 50 and 52 on opposite sides thereof to permit the cylindrical housing to be inserted cross-wise through the cylindrical central handle portion as shown in FIG. 5. Round flanges 54 and 56 extend outwardly from opposite axial ends of the central handle portion and are received within annular grooves 58 and 60 formed along inner surfaces of the cylindrical end caps 46 and 48 adjacent respective open ends of the end caps to permit rotation of the end caps about a central longitudinal axis 62 of handle portion 44. End caps 46 and 48 are of cup-like configuration and extend outwardly from respective open inner ends to outer ends closed by walls 64 and 66, respectively, of generally circular configuration oriented perpendicular to the longitudinal axis 62 of the central handle portion.

A fixed handle member 68 in the form of a finger loop 70 extends downwardly, looking at FIGS. 1 and 2, from the cylindrical side wall of end cap 46 at an acute angle relative to the proximal direction to accommodate one or more fingers of a user's hand. A movable handle member 72 includes a finger loop 74 disposed distally of fixed finger loop 70 and an arm 76 extending upwardly from the finger loop to a terminal end in the form of an internally splined sleeve or collar 78 of generally cylindrical configuration disposed within end cap 46 via an elongate slot 80 formed part way about the circumference of the cylindrical side wall of the end cap adjacent the point of attachment for finger loop 70. A transverse shaft 82 extends through splined sleeve 78 from a push button 84 disposed within a cylindrical recess formed in end cap wall 64 to a tubular sleeve or collar 86 with a smooth bore disposed within housing 12 perpendicular to the shaft. Transverse shaft 82 carries a bevel gear 88 of decreasing diameter in the direction of sleeve 86, the bevel gear being disposed between the smooth bore sleeve and the side wall of the housing. A spur gear 90 is carried on transverse shaft 82 within end cap 46. Spur gear 90 engages straight teeth or splines formed on an inner surface of sleeve 78 parallel to longitudinal axis 62 of the handle so that, among other things, pivotal movement of movable handle member 72 is translated into rotary movement of shaft 82. The movable handle member is preferably biased to move in a counterclockwise direction, looking at FIG. 2, toward fixed handle member 68, for example using a bias member 92 connected between the movable handle member and end cap 46. While a bias member in the form of a torsion spring is shown coiled around sleeve 78 in FIG. 5, it will be appreciated that other types of bias members can be used including, but not limited to, compression or expansion springs, leaf springs, rubber or magnets. Alternatively, the movable handle can be biased away from the fixed handle or configured for ratcheting or frictional movement.

Push button 84 is of a conventional type which, when pressed, alternatingly moves shaft 82 in the axial direction, along longitudinal axis 62 of the handle, between an engaged or depressed position where the first bevel gear 88 engages a second bevel gear 94 as shown by solid lines in FIG. 5 and a disengaged or elevated position, outwardly spaced from the extended position, where the first bevel gear is disengaged from the second bevel gear as shown by broken lines in FIG. 5. Spur gear 90 is disposed within end cap 46 and is of sufficient axial length to permit movement of the shaft in the axial direction while remaining at least partly engaged with splined sleeve 78 at the end of handle member 72. A tubular extension 96 extends radially outward from the smooth bored sleeve in the direction of bevel gear 88 to receive the inner terminal end of shaft 82 telescopically, the tubular extension being sufficiently long to accommodate axial movement of the shaft associated with operation of button 84. Shaft 82 extends through an elongate slot 98 formed part way about the circumference of housing sidewall 32 to permit rotation of handle 14 about the longitudinal axis of housing 12 as described in greater detail below.

Referring still to FIG. 5, second bevel gear 94 is mounted on an elongate drive shaft 100 extending longitudinally through the suturing instrument and is of decreasing diameter in the proximal direction to mesh with first bevel gear 88 when push button 84 is depressed or operated to move the first bevel gear to the engaged position. Drive shaft 100 is of hollow, tubular configuration and is oriented coaxial with longitudinal axis 24 of the suturing instrument to define central channel 22c. The drive shaft extends through smooth bored sleeve 86 to define an axis of rotation for the handle and terminates proximally at a rotational coupling 102 within housing 12 where the drive shaft connects telescopically with a tubular shaft extension 104, the tubular shaft extension preferably being fixed relative to a wall or walls of the housing so that it does not rotate or otherwise move with the drive shaft. Shaft extension 104 extends proximally from coupling 102 through housing rear wall 36 to a coupling 106, for example a Luer-type lock, for connection with sources of fluid or suction, operating units, or medical instruments and devices, with a valve 108 being disposed between the couplings to control passage of fluids and instruments through the central channel. The drive shaft is preferably formed of a medically acceptable plastic or metal material having a wall thickness sufficient to carry or form external threads at axially spaced locations within shaft 16 as shown at 110*a* and 110*b* in FIG. 5. As will be described in greater detail below, needle holders 18*a* and 18*b* are coupled with threaded portions 110*a* and 110*b* of the drive shaft such that handle members 68 and 72 can be used to control operation of their respective needle holding members.

Hereinafter, needle holder 18*a* will be referred to as a needle driver and needle holder 18*b* will be referred to as a needle catcher; it being understood that such designations are merely for purposes of clarity and that either needle holder can be used to drive a suture needle through anatomical tissue or to catch the end of the suture needle being driven in accordance with the present invention. Needle driver 18*a* and needle catcher 18*b* each include a pair of cooperating needle holding members mounted by the housing for rotation, the needle holding members of a given needle holder further being movable relative to one another to selectively grasp and release a suture needle or other objects during suturing procedures.

Needle holding members 112*a* and 114*a* of needle driver 18*a* are shown as a pair of pivotally opposed jaws in FIGS. 3A and 3B but can have other configurations for grasping and releasing a suture needle as well as for performing other functions during a surgical procedure. Jaws 112*a* and 114*a* are preferably formed at the distal end of an elongate tubular rod or body 116*a* as an integral one-piece unit to define a needle holding portion; however, it will be appreciated that the jaws can be formed separately from the tubular rod and attached thereto and that the tubular rod can be of solid configuration in cross section, if desired. As shown, however, the tubular needle holder rod 116*a* defines an elongate passage 118*a* through the needle holder which can be used as an additional or auxiliary operating channel providing access to the operative site from outside the body. Preferably, the tubular needle holder rod 116*a* will terminate proximally at a coupling (not shown) similar to coupling 106 and will be provided with a valve (not shown) disposed distally of the coupling to control access through the operating channel 118*a* of the needle holder. The jaws of the needle driver are preferably biased apart toward an open position, shown in FIG. 3A, where inner needle holding or grasping surfaces 120*a* and 122*a* are angularly spaced from one another. The lower jaw 114*a* in FIG. 3A is of fixed configuration and extends in parallel with a longitudinal axis 124*a* at the distal portion of the needle driver while the upper jaw 112*a* is pivotally movable between an open position, shown in FIG. 3A, where it extends outwardly from the longitudinal axis 124*a* of the needle driver distal portion at an angle and a closed position, shown in FIG. 3B, where it is in substantially parallel, abutting relation with the lower jaw. Opposed inner surfaces 120*a* and 122*a* of the jaws are shown with a plurality of longitudinally spaced teeth or ribs oriented perpendicular to the longitudinal axis 124*a* of the needle driver distal portion to securely hold a suture needle, tissue or other objects therebetween during a surgical procedure; however, the inner surfaces can have any suitable configuration for holding a suture needle and performing other functions including, but not limited to, configurations made up of spaced diamond-shaped protrusions, irregularly spaced teeth or ribs, and opposed arcuate portions which define a hole or opening when closed. As will be described in greater detail below, either jaw can carry a cutting member or biopsy box.

Referring to FIGS. 3A, 3B and 4, it can be seen that fixed jaw 114*a* of the needle driver is disposed between movable jaw 112*a* and central channel 22*c* so that, when the jaws of the needle driver and the needle catcher are in their respective open positions, the movable jaws will not contact one another or otherwise interfere with the movement of the other jaw. Under certain circumstances, however, it may be desirable to orient one or both of the needle driver and the needle catcher in a manner causing the movable jaw to be disposed inwardly of the fixed jaw, for example, by rotating the jaws 180° from the positions shown in FIG. 4. The tubular body or rod 116*a* of needle driver 18*a* is disposed telescopically within a flexible elongate outer member or sleeve 126*a* of tubular configuration which is axially movable relative to the rod between a retracted position, shown in FIG. 3A, where a distal end 128*a* of the flexible sleeve is proximally spaced from the jaws to allow them to open under the force of their own resilience and an extended position, shown in FIG. 3B, where the distal end of the flexible outer member slides over the jaws to cause them to close. The rod 116*a* and sleeve 126*a* of the needle driver cooperate to define an elongate proximal portion 130*a* of generally straight configuration extending through channel 22*a* in shaft 16 and a distal portion 132*a* with a predetermined deployed or working shape or condition where the distal portion bends outwardly at an angle relative to the longitudinal axis 125*a* of the proximal portion of the needle driver, the distal portion assuming the deployed shape or condition when the needle driver is in an axially extended position with the distal portion protruding distally beyond the distal end or face 42 of the shaft to define an outwardly angled arm as shown, for example, in FIGS. 7 and 8. The length and angular deflection of the distal portion of the needle driver are such that at least portions of jaws 112*a* and 114*a* are spaced laterally outward of a peripheral edge or diameter of the shaft 16 when the distal portion of the rod is in the deployed condition. Preferably, the distance between the axis of rotation 125*a* of the proximal portion of the needle driver and the position of needle holding surfaces 120*a* and 122*a* is approximately equal to the radius of curvature of the suture needle to be used so that the suture needle can be held between the needle holding surfaces and driven through anatomical tissue along an arcuate path having a radius of curvature substantially commensurate with the needle radius of curvature to minimize tissue trauma. The tubular rod is preferably stiffer than the sleeve but formed of an elastic material or with an elastic portion having elastic properties allowing the distal portion to bend inwardly, in a lateral direction relative to the longitudinal axis of the proximal portion of the rod so that, when the rod is axially retracted or moved proximally relative to the shaft, the distal portion will move laterally inward from the deployed working position shown in FIGS. 7 and 8 to the undeployed insertion position shown in FIGS. 1 and 2. In the axially retracted position, a sufficient amount of the distal portion of the needle driver is disposed within the shaft to cause the distal portion to straighten out or assume an undeployed shape or condition where the jaws do not protrude beyond the outer periphery or diameter of the shaft. If desired, however, the instrument can be modified to permit complete retraction of the needle driver (and/or the needle catcher) to a position where the jaws are proximally spaced from the distal end or face of the shaft as shown, for example, by broken lines in FIGS. 3A and 3B.

Tubular rod 116*a* of needle driver 18*a* carries a spur gear 134*a* adjacent a proximal end of collar 20*a*, the spur gear having straight teeth oriented parallel to longitudinal axis 125*a* of the proximal portion of the needle driver. An idler gear 136*a* is disposed between spur gear 134*a* and a sun gear 138*a* of epicyclic configuration formed along an inner surface of collar 20a adjacent the proximal end of the collar. Idler gear 136a includes a pair of face plates 140a and 142a of circular configuration which extend radially beyond the gear teeth to define a pair of lips or rims between which the spur gear and the epicyclic collar gear are disposed in order to maintain alignment of the gear system. Idler gear 136a is mounted on a pin 144a secured to a plate 146a extending upwardly, looking at FIG. 5, from the distal end of a tubular spacer 148a disposed telescopically around rod 116a adjacent spur gear 134a.

A push button 150a is disposed within a cylindrical recess 152a formed in an outer surface of collar 20a and includes a plunger or post 154a extending from the button through an elongate slot 156a formed part way about the circumference of the collar to a linear coupling block 158a disposed within shaft 16. Plunger 154a extends through a longitudinal slot 160a formed in block 158a to a cross member 162a wider than the slot so as to allow the block to slide transversely relative to the plunger while remaining attached to the plunger. Block 158a carries one or more external teeth 164a on a side facing threaded portion 110a of drive shaft 100 and defines a longitudinal opening or passage 166a therethrough with internal teeth 168a formed on an upper surface thereof looking at FIG. 5. The block is movable by operation of the button between an engaged position where teeth 164a meshingly engage threaded portion 110a of the drive shaft to cause the block to move linearly in response to rotation of the shaft and a disengaged position where the teeth 164a are radially or laterally spaced from the threaded portion such that the block is not moved in response to rotation of the shaft.

The outer tubular sleeve 126a of needle driver 18a extends through opening 166a in block 158a with lateral clearance and includes a round flange 170a extending radially outward therefrom between the block and spacer 148a and a rack made up of axially spaced rings or teeth 172a that extend around the portion of the sleeve disposed within the longitudinal block opening. Teeth 172a of the rack meshingly engage teeth 168a on the inner surface of the block opening when block 158a is in the engaged position shown in FIG. 5 such that axial movement of the block caused by rotation of shaft 100 is imparted to needle driver sleeve 126a thereby controlling the operation of jaws 112a and 114a as will be described in greater detail below.

A bias member 174a is disposed between spacer 148a and flange 170a to bias sleeve 126a distally relative to rod 116a so that jaws 112a and 114a are normally in a closed position. The bias member is shown as a helical spring coiled around rod 116a and held in compression between flange 170a and spacer 148a, however, any suitable bias member can be used including, but not limited to, tension springs, compression springs, helical springs, leaf springs, rubber and magnets.

Needle catcher 18b is shown as being identical to needle driver 18a, with needle holding members 112b and 114b in the form of opposed jaws mounted at the distal end of a tubular rod 116b slidably disposed within a sleeve 126b to define straight and angled portions 130b and 132b of the needle catcher. It will be appreciated, however, that the needle catcher can have any configuration for holding a needle and performing other operations. Tubular rod 116b of the needle catcher carries a spur gear 134b engaging an idler gear 136b disposed between the spur gear and a sun gear 138b formed about the inner circumference of collar 20b. The gears are substantially the same as those described for needle driver 18a, with the idler gear being mounted on a pin 144b secured to a plate 146b extending radially or laterally outward from a tubular spacer 148b fitted telescopically around tubular rod 116b. Push button 150b, which controls engagement of a linear coupling block 158b with threaded portion 110b of drive shaft 100, is similar to push button 150a with a plunger or post 154b extending therefrom through a slot 156b extending part way about the circumference of collar 160b and a longitudinal slot 160b formed in coupling block 158b to a cross member 162b slidably disposed within the block. Like coupling block 158a for needle driver 18a, coupling block 158b carries external teeth 164b on a side facing a threaded portion of the drive shaft and defines a longitudinal passage or opening 166b therethrough through which sleeve 126b of the needle catcher extends. Opening 166b includes teeth 166b on an inner surface thereof for engaging ring-like teeth 172b on the needle catcher sleeve. Like the needle driver, the jaws of the needle catcher are biased to a closed position by providing a bias member 174b between a flange 170b carried by the sleeve and spacer 148b. As best seen in FIG. 5, idler gears 136a and 136b as well as plungers 154a and 154b extend through longitudinal slots 176a and 176b formed through tubular member 30 of the shaft on diametrically opposed sides of the shaft to permit axial movement of the collar assemblies when push buttons 150a and 150b are operated to move blocks 158a and 158b to disengaged positions such as the position of block 158b shown in FIG. 5. Preferably, collars 20a and 20b will slide frictionally against or be coupled in ratching relation to shaft 16 so that, once the collars are moved to a desired axial location relative to the shaft, the collars will not move unless deliberately forced. If desired, a separate locking mechanism can be provided for each collar to maintain the axial and/or angular location of the collar relative to the shaft while permitting the collar to rotate about the longitudinal axis 24 of the shaft.

An electrical connector can optionally be mounted on the housing 12, as shown at 178 in FIG. 1, or at any other suitable location on the instrument including, but not limited to, the instrument handle or the proximal end of one of the channel-defining tubular shafts extending proximally from the housing, to connect electrically conductive elements of the instrument with a source of electricity for performing unipolar or bipolar procedures such as electric coagulation, for example using one or both of the jaws of a needle holder as conductive elements. In addition, an interior surface of any of the channels 22a–22e can be coated with an electrical and/or thermal insulating layer to permit safe insertion of electrical, thermal and/or other types of energy transmitting devices through the operating channels.

In use, instrument 10 is preferably grasped using finger loops 70 and 74 and, in the case of an endoscopic procedure, the instrument is guided to the operative site by a portal sleeve positioned in the wall of an anatomical cavity. The portal sleeve can be positioned in the anatomical cavity wall using any suitable penetrating technique, including those creating puncture sites by means of removable obturators, such as trocars, and can include a valve housing, if desired, to prevent loss of pneumoperitoneum during insertion and withdrawal of the instrument. The visualization of the endoscopic procedure can be accomplished using a conventional endoscope incorporated into the instrument, for example within the longitudinal operating channel 22e defined through shaft 16, or separately positioned within the anatomical cavity through a second portal sleeve located at another puncture site.

Prior to insertion, instrument 10 is preferably in the condition, state or position shown in FIGS. 3B and 4. More specifically, needle driver 18a and needle catcher 18b are preferably initially in axially retracted positions where respective distal portions of the needle holders are drawn at least part way into elongate shaft 16 and thus forced to move laterally inward in an elastic manner to undeployed positions where the needle holder jaws are spaced laterally inward of the peripheral edge of the shaft so as not to snag or catch on structure within the portal sleeve or valve housing during insertion. To this end, collars 20a and 20b are preferably initially disposed in the retracted positions shown in FIG. 2 with plungers 154a and 154b being disposed at the proximal ends of slots 176a and 176b in the shaft. Push buttons 150a and 150b on collars 20a and 20b, respectively, are preferably initially disposed in elevated positions so that the jaws of the needle driver and the needle catcher will be in closed or grasping positions with inner grasping surfaces of the jaws close together or abutting one another.

After insertion, needle driver 18a and needle catcher 18b are preferably moved distally relative to shaft 16 from the axially retracted, undeployed positions shown in FIG. 3B to the axially extended, deployed positions shown in FIGS. 7 and 8 by sliding collars 20a and 20b distally along longitudinal slots 176a and 176b. As the needle holders are advanced longitudinally, distal portions of the needle holders will no longer be restrained within the channels of the elongate shaft and will thus tend to recover elastically or move toward an undeformed shape or condition. More particularly, distal portions of the needle holders will spread apart or bend outwardly, away from the longitudinal axes of the channels from which they extend, toward deployed positions where the jaws of each of the needle holders are spaced laterally outward of the peripheral edge of the shaft. Under certain circumstances, however, it may be desirable for one of the needle holders to bend outwardly in the extended position while the other needle holder remains within the periphery of the outer tubular member or for one of the needle holders to be axially extended when the other is not.

A curved suture needle 180, preferably having a radius of curvature substantially commensurate with the distance between the axis of rotation of the needle holders and the deployed position of the needle holders, is positioned in needle driver 18a by moving jaws 112a and 114a apart from the closed position shown by solid lines in FIG. 8 to the open position shown by broken lines in FIG. 8, placing the body of the suture needle in the space between the jaws, and moving the jaws toward the closed position until grasping surfaces 120a and 122a of the needle driver abut the suture needle to hold it firmly in place.

Jaws 112a and 114a are moved to the open position by operation of handle members 68 and 72. If push button 84 of the handle is in the elevated or disengaged position shown by broken lines in FIG. 5, the push button is depressed to cause bevel gear 88 to move inwardly, in the direction of longitudinal axis 24, and into meshing engagement with bevel gear 94 mounted on drive shaft 100, as shown by solid lines in FIG. 5. Movable handle member 72 is then moved in a clockwise direction, looking at FIG. 2, away from fixed handle member 68 to cause internally threaded sleeve 78 to rotate in a clockwise direction. Spur gear 90 rotates with sleeve 78, causing shaft 82 to rotate in the clockwise direction with bevel gear 88. Bevel gear 94 is thus rotated in a counterclockwise direction, looking proximally, causing drive shaft 100, including threaded portions 110a and 110b, to rotate in a counterclockwise direction. Rotation of the drive shaft 100 can be converted into linear movement of the needle holder components by selectively depressing one or both of the buttons 150a and 150b mounted on collars 20a and 20b. Depression of the buttons causes blocks 158a and 158b to move inwardly, toward the drive shaft, such that teeth 164a and 164b mesh with or engage the threaded portions 110a and 110b, respectively, of the drive shaft. Coupling blocks 158a and 158b move linearly in the proximal direction along the drive shaft as the drive shaft rotates in the counterclockwise direction, with the plungers 154a and 154b sliding axially within the slots 160a and 160b formed through the blocks. In the depressed or engaged condition shown at the top of FIG. 5, the teeth or rings 172a of the needle driver sleeve 126a engage teeth 168a inside the block opening 166a such that the needle driver sleeve 126a moves linearly with the block in the proximal direction relative to rod 116a. The distal end 128a of the sleeve 126a is thus moved proximally relative to the jaws, allowing the jaws to spread apart or move toward the open position shown in FIG. 3A under the influence of their own elasticity or resilience. The needle 180 is then placed between grasping surfaces 120a and 122a of the needle driver with the body of the needle being oriented transverse to the longitudinal axis of the distal portion of the needle and the sharp, tissue penetrating tip 182 of the needle being circumferentially aligned with and angularly spaced from the jaws of needle catcher 18b. With needle 180 positioned between jaws 112a and 114a of needle driver 18a, movable handle member 72 is released or otherwise caused to move in a counterclockwise direction, looking at FIG. 2, in response to finger pressure and/or the spring bias provided by bias member 92. As the movable handle member 72 moves counterclockwise, transverse shaft 82 is also caused to move counterclockwise thereby carrying bevel gear 88 in the counterclockwise direction. Bevel gear 94 is thus caused to move in a clockwise direction, looking proximally along longitudinal axis 24, so that drive shaft 100 is driven clockwise, causing block 158a to move in the distal direction relative to rod 116a such that distal end 128a of the sleeve moves distally relative to the rod and into camming contact with the jaws 112a and 114a, causing the jaws to move toward one an other and into gripping contact with the body of needle 180 as shown by solid lines in FIG. 8. Needle 180 is thus held securely between jaws 112a and 114a and will move with the needle driver 18a during the suturing procedure. If the force biasing the jaws to a closed position is not sufficient to hold a suture needle between the jaws in a desired positioned during suturing procedures, finger loops 70 and 74 can be squeezed tightly together and locked in place by ratchet members 186 and 188 mounted in opposed relation on the handle members.

Figure 9:
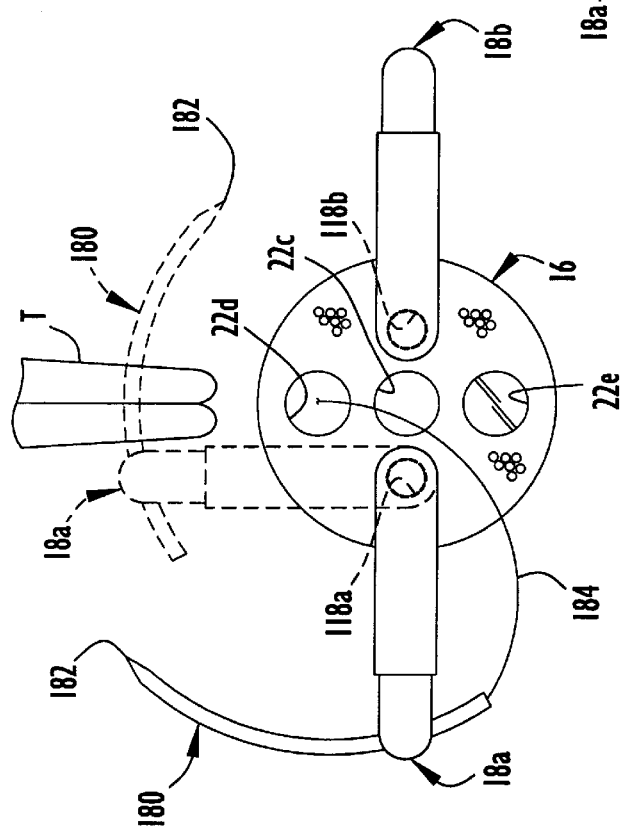

At this point, needle driver 18a and needle catcher 18b extend outwardly from shaft 16 of the suturing instrument in diametrically opposite directions as shown in FIG. 9. Anatomical tissue T is positioned between tip 182 of needle 180 and needle catcher 18b with a length of filamentous suture material 184 being shown attached to the proximal end of the needle for purposes of illustration only. Needle 180 is driven through tissue T by rotating collar 20a in a counterclockwise direction, looking at FIG. 6, so that idler gear 136a is also moved in a counterclockwise direction to drive spur gear 134a in a clockwise direction. Clockwise movement of spur gear 134a causes the proximal portion of needle driver 18a to rotate clockwise within channel 22a such that jaws 112a and 114a at the distal end of the needle driver are caused to move along a first arcuate path coaxial with longitudinal axis 125a of the proximal portion but having a radius of curvature approximately equal to or substantially commensurate with the radius curvature of the needle until the tip 182 of needle 180 is caused to penetrate through the anatomical tissue T and be disposed at a location on the opposite side of the tissue as shown by broken lines in FIG. 9. Button 150a can be pressed prior to rotating collar 20a or after the collar has been rotated to lift switching block 158a away from drive shaft 100 so that jaws 112a and 114a will remain closed due to the distal bias on sleeve 126a regardless of any subsequent manipulation of the handle members.

Figure 10:
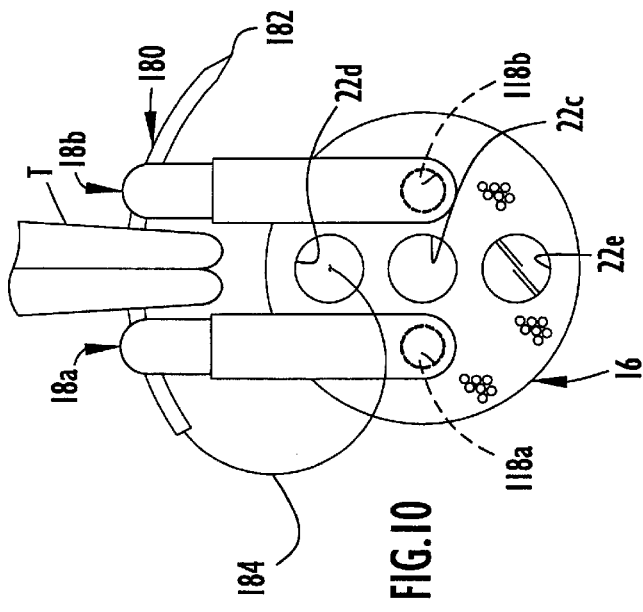
FIGS. 9–11 are front views of a suturing instrument illustrating a method of suturing anatomical tissue in accordance with the present invention.

Needle catcher jaws 112a and 114a are then opened by pushing button 150b on collar 20b to cause block 158b to engage threaded portion 110b of drive shaft 100 and by moving handle member 72 in a clockwise direction, looking at FIG. 2, away from fixed handle member 68. As described above, clockwise rotation of handle member 72 causes drive shaft 100, including threaded portion 110b, to rotate in a counterclockwise direction. Coupling block 158b moves linearly in the proximal direction along the drive shaft as the drive shaft rotates in the counterclockwise direction, causing needle catcher sleeve 126b to move linearly with the block in the proximal direction relative to rod 116b. The distal end 128b of the sleeve 126b is thus moved proximally relative to the jaws, allowing the jaws to spread apart or move toward the open position shown in FIG. 3A under the influence of their own elasticity or resilience. Needle catcher 18b is then rotated in a counterclockwise direction, looking at FIG. 9, from a first position oriented substantially perpendicular to the needle driver to a transfer position oriented substantially parallel to the needle driver as shown in FIG. 10. Alternatively, needle catcher 18b can be rotated to the transfer position prior to or simultaneously with rotation of the needle driver to serve as a support or backing for the tissue as the needle penetrates. Counterclockwise rotation of the needle catcher can, for example, be accomplished by rotating collar 20b in a clockwise direction, looking proximally, to cause idler gear 136b to be driven in a clockwise direction by sun gear 138b and spur gear 134b to be driven in the counterclockwise direction.

Figure 11:
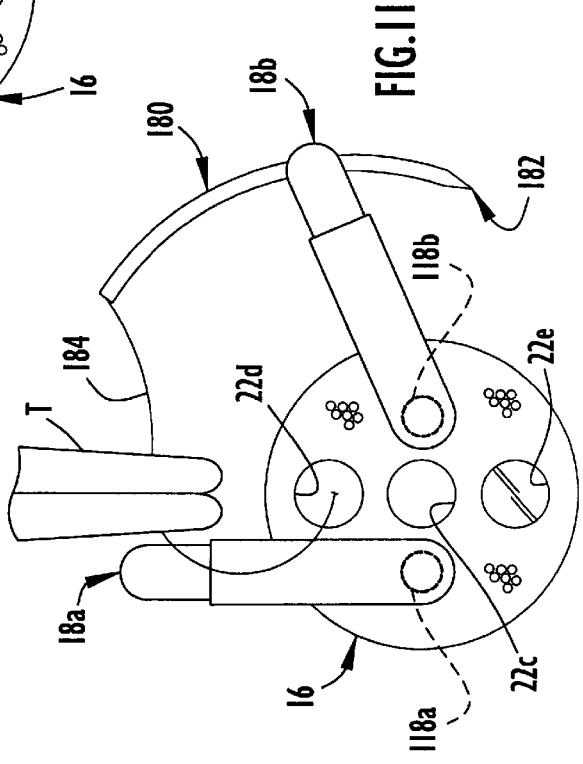

When suture needle 180 is disposed between jaws 112b and 114b of the needle catcher 18b, finger pressure on handle members 68 and 72 is reduced to allow bias member 92 to move needle catcher sleeve 126b distally to close the jaws. Button 150b on collar 20b is then pushed to disengage block 158b from threaded portion 110b of drive shaft 100, and button 150a on collar 20a is pushed to cause block 158a to engage threaded portion 110a of the shaft. Handle member 72 is then rotated in a clockwise direction, looking at FIG. 2, to open jaws 112a and 114a of the needle driver as described above, thereby transferring possession of suture needle 180 to the needle catcher. Jaws 112a and 114a of the needle driver are preferably held in the open position, either manually or by means of a latching mechanism or lock, as the needle catcher 18b is rotated in a clockwise direction, looking at FIG. 10, to pull the suture needle 180 through the tissue T along a second arcuate path coaxial with longitudinal axis 125a of the needle catcher and having a radius of curvature approximately equal to or substantially commensurate with the radius of curvature of the needle to minimize tissue trauma. At this point, the length of suture material 184 can be knotted to form a single stitch or another stitch can be made by moving the instrument away from the tissue and performing the above steps in reverse order to transfer the suture needle back to the needle driver, after which the suture needle is driven through the anatomical tissue at a second site or location in the manner described above. Alternatively, the suture needle can be left between the jaws of the needle catcher and the instrument manipulated to position the tissue T between the needle catcher and the needle driver, after which the needle catcher can be rotated clockwise, looking at FIG. 11, to cause the suture needle to penetrate through the tissue. The needle driver is rotated counterclockwise, looking at FIG. 11, to receive the suture needle so that the suture needle may be grasped by the needle driver and released from the needle catcher to be pulled completely through the tissue with clockwise rotation of the needle driver, the needle having essentially made a complete revolution about the central longitudinal axis of the instrument. In the latter technique, the suture needle 180 may need to be advanced circumferentially in the clockwise direction in order for the tip 182 to protrude sufficiently from the needle catcher for additional stitches to be formed. Such repositioning can, for example, be accomplished by grasping the proximal end of the needle with the needle driver or a separate needle holding instrument and releasing the needle holding members of the needle catcher to allow manipulation of the needle to a position in the needle catcher wherein the tip of the needle protrudes sufficiently to pass through the anatomical tissue and be captured by the needle driver.

The suturing instrument can also be used to suture anatomical tissue in the manner shown in FIGS. 12–14 wherein the needle driver 18a is rotated clockwise, from the initial or first position shown in FIG. 9, to the transfer position shown in FIG. 10, and the needle catcher 18b is either left in the initial position shown in FIG. 9 or rotated clockwise, looking at FIG. 9, from the initial position to a pull-through position angularly spaced from the tip of a suture needle 180 held by the needle driver. The needle catcher 18b could also be rotated in a counterclockwise direction, looking at FIG. 12, toward the transfer position shown in FIG. 10 so long as it remains angularly spaced from the tip of the suture needle to permit tissue T to be placed between the tip of the suture needle and the needle catcher. In FIG. 12, for example, needle driver 18a is shown in the transfer position oriented about 90° clockwise from the initial position shown in FIG. 9, and needle catcher 18b is shown in a pull-through position oriented about 90° clockwise from the initial position shown in FIG. 9.

Prior to suturing, button 150a is preferably pressed to disengage the needle driver from drive shaft 100 so that the suture needle is held between the jaws of the needle driver under the influence of the force biasing the needle driver jaws together, while button 150b is operated or pressed to engage the needle catcher with the drive shaft so that the jaws of the needle catcher may be opened by operation of handle members 68 and 72. Shaft 16 is then rotated in a clockwise direction, looking at FIG. 12, about the longitudinal axis 24 of the shaft, for example by rotating handle 14 with a twisting movement of the user's wrist and allowing the instrument housing to rotate with the handle, to drive the suture needle 180 through tissue T in a clockwise direction as shown in FIG. 13, preferably along an arcuate path having a radius of curvature substantially commensurate with the radius of curvature of the needle. Needle catcher 18b is also moved along an arcuate path in a clockwise direction about the longitudinal axis of shaft 16 as the entire suturing instrument is rotated and may need to be moved counterclockwise, looking at FIG. 13, in an arcuate manner to receive the body or tip of the suture needle, for example by rotating collar 20b in a clockwise direction relative to the shaft while holding the needle driver stationary, as shown in FIG. 14. Handle members 68 and 72 are then operated to close the jaws of the needle catcher against suture needle 180 so that the suture needle is securely held by the needle catcher, after which button 150b is pressed to disengage the needle catcher from drive shaft 100 and button 150a is pressed to engage needle driver 18a with the drive shaft. The jaws of needle driver 18a are then opened to release the suture needle from their grasp by causing handle members 68 and 72 to move apart. Collar 20b is then rotated counterclockwise, looking proximally, to cause needle catcher 18b to rotate clockwise as shown by broken lines in FIG. 14, thereby pulling suture needle 180 through the tissue. The instrument may then be moved away from the anatomical tissue slightly so that the suture needle can be transferred back to needle driver 18a by rotating needle catcher 18b in a counterclockwise direction, looking at FIG. 14, until the proximal end or body of the suture needle is received between the jaws of the needle driver. Needle catcher 18b is then operated to release the suture needle at about the same time needle driver 18a is operated to grasp the suture needle. The needle driver and needle catcher are then rotated in counterclockwise and clockwise directions, respectively, to the positions shown in FIG. 12 (or any other suitable positions) so that the suturing instrument can be used to apply another stitch to the anatomical tissue in the manner described above.

At any point during the surgical procedure, operating channels 22a–22e can be used for irrigation or aspiration of the surgical site and can serve as a space for holding the suture material or as a portal for the introduction of other medical instruments and devices such as, for example, forceps, cutting members, needles and endoscopes. Knotting elements can also be introduced at the operative site via the operating channels for use in leu of or in addition to traditional knotting techniques during the suturing procedure. Some examples of suitable knotting elements for this purpose are described in pending application Ser. Nos. 08/366,285, filed Dec. 29, 1994; 08/377,723, filed Jan. 25, 1995; 08/401,002, filed Mar. 9, 1995; and 08/585,875, filed Jan. 16, 1996; the disclosures of which are incorporated herein by reference.

FIG. 8 illustrates a further use of one of the operating channels 22a–22e wherein a ligating device, shown by broken lines at 190, is advanced distally through one of the channels, for example central channel 22c, to assist in tying a suture. The device 190 is of the conventional ENDOLOOP-type and includes an elongate tubular pusher 192 and a length of filamentous ligature material 194 extending through the pusher to define a loop 196 with a knotting element 198 in the form of a pretied knot at the distal end of the pusher. For purposes of illustration, a free end of the ligature material is shown attached to the proximal end of suture needle 180 so that, after the suture needle has been pulled through anatomical tissue with the ligature material, the needle can be passed through the loop and the loop can be tightened to control the tension of the suture.

In addition to operating channels 22a–22e, auxiliary operating channels can be defined through one or both of the needle driver 18a and the needle catcher 18b as shown by broken lines at 118a and 118b in FIGS. 9–14 to provide access to the operative site from outside the anatomical cavity. The auxiliary operating channels can terminate distally at openings adjacent the jaws of the needle holders or at openings defined at the bend connecting straight and angled portions of the needle holders.

It will also be appreciated that when push button 84 is in the elevated, undepressed position shown by broken lines in FIG. 5, shaft 82 slides outwardly within tubular extension 96, moving bevel gear 88 away from bevel gear 94 so that end cap 46 may be rotated about an axis transverse to the longitudinal axis of shaft 16 to move handle members 68 and 72 between the transverse position shown by solid lines in FIG. 2 and the rearward facing position shown by broken lines in FIG. 2. Push button 84 may then be depressed to maintain the handle members in the desired angular orientation. The handle members 68 and 72 can also be rotated about the longitudinal axis of the shaft 16 by moving push button 84 to the elevated, undepressed position and rotating the entire handle portion 14 about the housing 12, for example by grasping the housing with one hand while moving the handle with the other hand. When a desired angular orientation is achieved, push button 84 may be depressed so that the bevel gear 88 is made to engage bevel gear 94, thereby locking the handle in place relative to the housing.

While the needle driver and the needle catcher have been described above as being independently controlled by operating mechanisms such as push buttons and collars which, for the most part, must be operated with both hands, it will be appreciated that a single operating mechanism can be used to synchronize movement of the needle driver and the needle catcher relative to one another as well as operation of their respective needle holding members to further simplify the suturing process by allowing one-hand operation of the instrument. For example, in FIGS. 15–18, a modification of the suturing instrument is shown wherein proximal portions of the modified needle driver 1018a and needle catcher 1018b extend through hollow cylindrical guide members 1200a and 1200b disposed within the instrument housing 1012. Cylindrical guide members 1200b and 1200b extend inwardly from opposite sides of housing side wall 1032 in longitudinally spaced relation. A shaft 1082 extends transversely between cylindrical guide members 1200a and 1200b and is coupled with movable handle member 1072 to rotate when the handle member is pivotably moved about the longitudinal axis of the shaft. The shaft 1082 carries a first bevel gear 1088a spaced inwardly of needle catcher 1018b and a second bevel gear 1088b spaced inwardly of needle driver 1018a. Needle driver 1018a extends coaxially through cylindrical guide member 1200a and carries a bevel gear 1094a meshingly engaging the second bevel gear 1088b on shaft 1082. Needle catcher 1018b extends coaxially through cylindrical guide member 1200b and carries a bevel gear 1094b. An idler gear 1202 is mounted between needle catcher bevel gear 1094b and shaft-mounted bevel gear 1088a to reverse the direction of the rotary movement imparted to the needle catcher from the shaft. Inner members or rods 1116a and 1116b of the needle holders carry pins 1204a and 1204b, respectively, which extend radially outward from the inner tubular members through longitudinal slots 1206a and 1206b formed in outer needle holder sleeves 1126a and 1126b. Pins 1204a and 1204b are received within grooves or tracks 1208a and 1208b formed along inner surfaces of the cylindrical guide members 1200a and 1200b, respectively. Tracks 1208a and 1208b are of generally U-shaped configuration with proximal and distal legs 1210a and 1210b of generally parallel configuration oriented transverse to the longitudinal axis of the needle holders and a curved portion or bend 1212 connecting ends of the legs. The legs of track 1208a for the needle driver extend counterclockwise from the bend, looking proximally, while the legs of track 1208b for the needle catcher extend clockwise from the bend in a direction opposite the legs of the needle driver track. An optional bias member 1214 is also shown connected between inner needle catcher member 1116b and outer needle catcher member 1126b to bias the needle holding members to a desired position relative to one another. A similar bias member can optionally be connected between the inner needle driver member 1116a and the outer needle driver member 1126a, if desired.

In use, handle members 1068 and 1072 are preferably biased away from one another to an open position with needle holding members of the modified needle driver 1018a preferably initially being in the closed position to grasp a suture needle when pin 1204a is at the terminal end of proximal leg 1210b of the needle driver track as shown in FIG. 15, and with needle holding members of the modified needle catcher 1018b preferably initially being in the open position to receive a suture needle when pin 1204b is at the terminal end of distal leg 1210a of the needle catcher track. When handle members 1068 and 1072 are squeezed together, shaft 1082 is rotated counterclockwise, looking upwardly along the shaft in FIG. 15, causing bevel gears 1088a and 1088b mounted on the shaft to rotate in the counterclockwise direction. Shaft-mounted bevel gear 1088b drives bevel gear 1094a on the needle driver 1018a in a clockwise direction, looking proximally, with inner member 1116a of the needle driver being keyed to move with the outer sleeve 1128a so that pin 1204a slides along track 1208a in the cylindrical guide member 1200a. As needle driver 1018a rotates in the clockwise direction, pin 1204a slides upwardly, looking at FIG. 15, along proximal leg 1210b but does not move axially a significant amount until it reaches bend 1212 where it moves distally slightly beyond the apex of the bend to be disposed on the side of the bend closest distal leg 1210a. Distal movement of the pin at the bend causes the jaws to open at about the same time the needle driver is rotated into the transfer position shown by broken lines in FIG. 9. Counterclockwise rotation of shaft-mounted bevel gear 1088a causes idler gear 1202 to rotate clockwise, looking upwardly along the shaft in FIG. 15, in a direction opposite the direction of rotation of the shaft. Idler gear 1202 drives bevel gear 1094b on the needle catcher 1018b counterclockwise, looking proximally, in a direction opposite the direction of rotation of needle driver 1018a. As needle catcher 1018b rotates in the counterclockwise direction, pin 1204b slides downwardly, looking at FIG. 15, along distal leg 1210a but does not move axially a significant amount until it reaches bend 1212 where it moves proximally slightly beyond the apex of the bend to be disposed on the side of the bend closest proximal leg 1210b. Proximal movement of the pin at the bend causes the jaws of needle catcher 1018b to close at about the same time the needle catcher is rotated into the transfer position shown in FIG. 10. It will be appreciated, therefore, that squeezing of the handles with one hand causes a suture needle originally held by the needle driver to be moved arcuately through anatomical tissue and to be subsequently released from the needle driver and grasped by the needle catcher.

Releasing handle members 1068 and 1072 causes bias member 1092 to move handle member 1072 in a clockwise direction, looking upwardly along the shaft in FIG. 15, so that shaft 1082 is moved in a clockwise direction. Clockwise rotation of the shaft results in counterclockwise rotation of needle driver 1018a, looking proximally, and simultaneous clockwise rotation of needle catcher 1018b, looking proximally. As needle driver 1018a rotates in a counterclockwise direction, pin 1204a moves downwardly, looking at FIG. 15, along distal leg 1210a of the track without moving axially so that jaws of the needle driver remain in the open position. As needle catcher 1018b rotates in the clockwise direction, pin 1204b moves upwardly, looking at FIG. 15, along proximal leg 1210b of the track without moving axially so that jaws of the needle catcher remain in the closed position to hold the suture needle as it is pulled through the tissue. Squeezing the handle members again and subsequently releasing them reverses the above process so that the suture needle is transferred back to the needle driver to apply another stitch to the anatomical tissue in the manner described above.

FIGS. 19 and 20 show a modification of a needle holder for use with the suturing instrument according to the present invention wherein the modified needle holder 2018 includes a pair of jaws to 2112 and 2114 pivotably mounted on a pair of pins 2216a and 2216b secured to diametrically opposed sides of a hollow tubular rod or sleeve 2116 telescopically fitted within an outer tubular sleeve 2126, the tubular rod defining an auxiliary operating channel 2118 providing access to the operative site from outside the anatomical cavity. Jaws 2112 and 2114 are biased apart toward the open position shown in FIG. 19, for example using a torsion spring (not shown) coiled around one of the pins and connected between the jaws or a pair of spring members (not shown) held in compression between each jaw and the hollow tubular rod, and the jaws are movable inwardly toward one another against the spring bias in response to distal movement of outer tubular sleeve 2126 against the rear or back edges of the jaws. If desired, jaws 2112 and 2114 can be mounted on a single pin or pivot extending diametrically across the width of sleeve 2116; however, use of separate pivots provides a substantially unobstructed passage through the operating channel.

Any of the needle holding members described herein can carry a biopsy box or a cutting member such as the blade shown by broken lines at 2220 in FIG. 19. Blade 2220 is oriented perpendicular to the inner grasping surface of upper jaw 2112 and extends downwardly, looking at FIG. 19, from the inner grasping surface to fit within a cooperatively configured pocket or recess 2222 formed in lower jaw 2114 when the jaws are closed together. Examples of other cutting members which can be used are shown and described in U.S. patent application Ser. No. 08/612,634, filed Mar. 4, 1996, and Ser. No. 08/376,186, filed Jan. 20, 1995, the disclosures of which are incorporated herein by reference.

The modified needle holder 3018 shown in FIG. 21 is similar to the needle holders shown in FIGS. 1–14 but with both jaws 3112 and 3114 being pivotably movable between normally open positions extending laterally outward from the tubular rod 3116 at acute angles and closed positions wherein the jaws abut one another. A pair of cams 3224a and 3224b are also shown extending outwardly from the jaws adjacent the distal end 3128 of outer sleeve 3126 to provide additional force when closing the jaws together. An optional cutting member in the form of a blade 3220 and a cooperatively configured pocket or recess 3222 are also shown.

Yet another modified needle holder is shown in FIGS. 22 and 23 at 4018 and includes a first needle holding member 4112 in the form of an outer tubular sleeve 4126 with a lateral cut-out or window 4226 having a grasping surface 4120 formed on a proximal-facing surface or face of the window and a second needle holding member 4114 in the form of an inner tubular sleeve 4116 fitted telescopically within the outer tubular sleeve and having a grasping surface 4122 formed along a peripheral edge of the inner member to operate cooperatively with the grasping surface at the distal end of the outer member to hold a suture needle or other objects within the window. An auxiliary operating channel, shown by broken lines in FIG. 23 at 4118, may optionally be formed through the inner and outer members of the needle holder to permit access to the operative site via the channel from outside the body. If an auxilliary operating channel is not needed or desired, the second needle holding member 4114 can be solid instead of tubular, thus presenting a wider grasping surface if desired.

The window 4226 in the outer tubular sleeve 4126 of the modified needle holder 4018 can be oriented to face any suitable direction relative to the central longitudinal axis of the shaft 16 dependent upon the shape of the suture needle and procedural use. For example, in FIG. 24, a pair of needle holders 4018a and 4018b identical to the needle holder shown in FIGS. 22 and 23 are oriented such that their respective windows 4226a and 4226b face inwardly, toward the central longitudinal axis 24 of the suturing instrument. By directing the windows inwardly, the process of loading a suture needle into one of the needle holders from an operating channel defined through the shaft can be simplified. In FIG. 25, on the other hand, needle holders 4018a and 4018b are oriented such their respective windows 4226a and 4226b face outwardly, away from the central longitudinal axis of the suturing instrument, possibly to receive a suture needle from a recess or channel formed along an outer peripheral edge of the shaft.

FIG. 26 shows still another modification of a needle holder for use with the suturing instrument according to the present invention wherein the modified needle holder 5018 includes a first needle holding member 5112 in the form of a hook and a second needle holding member 5114 in the form of a keeper movable relative to the hook to capture and release a suture needle placed within the hook. The needle holding members are preferably formed of flat strips of a medically acceptable material, such as stainless steel, configured to lay flat against one and other to permit relative sliding movement of the needle holding members. The first needle holding member 5112 includes an elongate portion or leg 5228 extending distally from within the instrument housing to a bend 5230 where the first needle holding member folds inwardly upon itself to form a short leg 5232 parallel to the elongate portion or leg of the needle holding member thereby defining a hook with a proximal-facing mouth 5233 having a gap width suitable for receiving the shaft or body of a suture needle. The second needle holding member 5114 is slidingly disposed along the first needle holding member 5112 and includes a distal end 5234 configured to fit within the mouth of the hook as a keeper, the distal end of the second needle holding member being shown with an optional scalloped edge having one or more curved recesses. The first or second needle holding member may also be formed with a cutting member such as a blade or a notch of generally V-shaped configuration defined along an edge of the needle holding member and having one or more sharp edges to cut lengths of suture material received therein under pressure as shown, for example, by broken lines at 5236 in FIG. 26. The first needle holding member is also shown with optional slots or openings 5238a and 5238b formed on opposite sides of the hook to permit straight or slightly curved suture needles to be placed perpendicularly through short and long legs of the hook so as to be oriented radially relative to the longitudinal axis of the shaft. The slotted openings extend transversely, relative to a longitudinal axis of the needle holder, from respective open ends disposed along a lateral or longitudinal edge of the first needle holding member to generally centrally located terminal tends of rounded or semi-circular configuration with a size to receive the body or shank of a suture needle extending transversely through legs of the hook. As mentioned above, the scalloped edge at the distal end of the second needle holding member or keeper 5114 is configured with laterally spaced recesses, one of which is preferably aligned with a terminal portion or end of the slotted openings to cradle the needle positioned within the openings in a manner to secure the needle during linear suturing procedures wherein the suture needle is passed back and forth between the needle holders via lateral movement, for example as described in patent application Ser. No. 08/758,648, filed Nov. 27, 1996, the disclosure of which was incorporated by reference hereinabove.

The modified needle holder 5018 shown in FIG. 26 can be positioned within the shaft 16 of the suturing instrument to orient the mouth 5233 of the hook formed at the distal end of the needle holding member 5112 to face any suitable direction relative to the central longitudinal axis 24 of the shaft dependent upon the shape of the suture needle and procedural use. For example, in FIG. 27, a pair of needle holders 5018a and 5018b identical to the needle holder shown in FIG. 26 are oriented such that the mouths 5233a and 5233b of their respective hook-like members 5112a and 5112b face inwardly, toward the central longitudinal axis 24 of the suturing instrument, for example to facilitate loading a suture needle into one of the needle holders from an operating channel defined through the shaft. In FIG. 28, on the other hand, needle holders 5018a and 5018b are oriented such their respective mouths 5233a and 5233b face outwardly, away from the central longitudinal axis of the suturing instrument, possibly to receive a suture needle from a recess or channel formed along an outer peripheral edge of the shaft.

Still another modification of a needle holder for use with the suturing instrument according to the present invention, as shown in FIGS. 29 and 30, includes a pair of needle holding members 6112 and 6114 in the form of jaws extending distally from a pair of crossed arms 6240a and 6240b connected by a pivot 6242 located medially along the lengths of the arms. A pair of elongate linkages 6244a and 6244b extend inwardly from pivots 6246a and 6246b at respective proximal ends of the arms to a pivot 6248 connecting the linkages with an elongate rod 6250. Linkages 6244a and 6244b are disposed on opposite sides of the rod, with pivot 6248 extending through the linkages and the rod and with tabs or ears 6252 extending laterally outward from the rod in opposite directions to overhang the linkages as stops preventing the linkages from spreading outwardly beyond a predetermined position. Jaws 6112 and 6114 are moved relative to one another by moving the outer tubular member and rod relative to one another. The jaws are normally biased apart, for example by a torsion spring coiled around a pivot and connected between the jaws, and are closed by moving the outer tubular member distally relative to the jaws, for example by advancing the outer tubular member distally and/or pulling the rod in the proximal direction. In a preferred embodiment, the outer tubular member is biased distally relative to the jaws so that the jaws are normally in a closed position.

From the above, it will be appreciated that the suturing instrument according to the present invention permits suturing of anatomical tissue during endoscopic procedures without the need of having to use multiple needle holding instruments inserted through multiple puncture sites by inserting an elongate shaft carrying a needle driver and a needle catcher through a single puncture site. Preferably, the needle driver and the needle catcher each include a distal portion movable between an undeployed, contracted or parked position spaced laterally inward of a peripheral edge of the elongate shaft to facilitate insertion through a portal sleeve and a deployed, expanded or working position where at least part of the distal portion is spaced laterally outward of the peripheral edge of the elongate shaft to permit use of suture needles having radii of curvature equal to or larger than a radial or lateral dimension of the elongate shaft and to permit suturing of thicker tissue by increasing the space between the needle driver and needle catcher. The elongate shaft is mounted by a handle with controls for moving one or both of the needle driver and the needle catcher axially and in a rotary manner. The needle driver and the needle catcher each include needle holding members selectively operable to grasp and release a suture needle so that, when the needle holding members of the driver are operated to grasp the suture needle, the driver can be moved in a direction to drive the suture needle through anatomical tissue positioned between the driver and the catcher, and when the needle holding members of the catcher are operated to grasp the suture needle, the needle holding members of the driver can be operated to release the suture needle, thereby allowing the catcher to be moved in a direction to pull the suture material through the anatomical tissue. Movement of either needle holder can be accomplished by rotating the needle holder relative to the elongate shaft or by rotating the needle holder with the elongate shaft as a unit.

The needle driver and the needle catcher of the suturing instrument can be of the same or different design so long as each is a needle holder including one or more needle holding members capable of grasping and releasing a needle. The needle holders can be configured to hold needles of any size or shape including, but not limited to, needles with straight or curved bodies, and the needle holders are preferably mounted to permit movement of the needle holding members relative to one another in directions causing the needles to be passed or transferred from one needle holder to the other. While the needle holders are shown disposed within cylindrical channels formed through the elongate shaft, it will be appreciated that one or more of the needle holders can be disposed within arcuate channels so that, for example, one of the needle holders can be moved arcuately within the shaft about the center of curvature of the curved channel while the other needle holder is rotated about its longitudinal axis or vice versa. Distal portions of the needle driver and the needle catcher preferably extend laterally outward at an angle from respective longitudinal axes of the elongate shaft to carry the needle holding members so that, when the needle holders are rotated about their respective longitudinal axes, the needle holding members are made to move arcuately along non-concentric arcuate paths which may or may not intersect dependent upon the shape and size of the suture needle used. Any type of needle holder can be modified for use with the suturing instrument according to the present invention by configuring a distal portion of the needle holder to be normally bent outwardly at an angle relative to the proximal portion, including, but not limited to, any of the needle holders described in U.S. patent application Ser. No. 08/758,648, filed Nov. 27, 1996, and Ser. Nos. 08/847,182, 08/847,254, 08/847,253, 08/847,189, and 08/847,252, filed May 1, 1997, the disclosures of which are incorporated herein by reference. For example, any of the needle holders can include a transverse connecting member extending perpendicularly outward from a proximal portion of the needle holder to needle holding members laterally offset from the proximal portion.

One or more lengths of suture material can be attached to each suture needle at any desirable location along the body of tip of the needle including, but not limited to, the proximal end of the needle, intermediate or medial portions of the needle body, or locations adjacent the tip of the needle. It will also be appreciated that the suturing instrument according to the present invention can be used with suture needles having sharp or blunt tissue penetrating tips, and needles having tissue penetrating tips at opposite axial ends of a needle body.

The needle holding members of the needle catcher and the needle driver shown and described herein are exemplary of the types of needle holding members that can be used according to the present invention. Accordingly, the needle holding members can have any suitable configuration for individually or cooperatively grasping needles to suture anatomical tissue including, but not limited to, jaw-like configurations wherein the needle holding members pivot, slide or otherwise move relative to one another to capture and release a needle. The needle holding members can be of straight, curved or angled configuration and can be provided with ribs, grooves, slots and/or holes along grasping surfaces to assure a positive grip. The needle holding members can also carry cutting members, such as slots with sharp edges or protruding blades, and can have opposed arcuate or concave portions for clamping tubular objects, such as organs, without compressing the objects, as well as portions configured to take a tissue sample for biopsy. When the needle holding members are carried at the distal end of one or more elongate components, for example a rod telescopically fitted within a tube, either component can include a distal portion of predetermined shape which, in an unrestrained condition, bends laterally outward at an angle relative to the longitudinal axis of the proximal portion of the needle holder component. Furthermore, components of a needle holder can be keyed or coupled to move together so that, for example, if one of the components is rotated the other component will be rotated as well.

The needle driver and the needle catcher of the present invention can also be used alone or in combination as end effectors to perform lysis of adhesion, dissection, pickup and cutting, pickup and clipping, pickup and suturing with a suture needle, unipolar and bipolar electrosurgery, and numerous other procedures. Although the suturing instrument is shown and described herein as having two needle holders, it will be appreciated that one or more than two needle holders can be used dependent upon the procedure to be performed and the preference of the user. Also, the needle holders can be positioned at diametrically opposed locations relative to the central longitudinal axis of the elongate shaft as shown or at any other laterally spaced positions.

Although the elongate shaft is shown as being composed of optical fibers disposed within a tubular sleeve, it will be appreciated that the elongate shaft can be formed without a separate sleeve, for example by embedding or molding the optical fibers within a medically acceptable polymer matrix or by adhesively connecting the fibers together. The elongate shaft can also be formed without optical fibers extending therethrough, in which case a light source may be inserted through one of the channels defined through the shaft or through a separate puncture to illuminate the operative site. The shaft can be rigid or flexible and can be made of any suitable medically acceptable material, such as plastic or stainless steel. The cross-sectional configuration of the outer surface of the shaft is preferably circular as shown but can be elliptical, polygonal or have any other configuration suitable for a particular purpose. The distal end or face of the shaft can be flat as shown, convex or concave; and, when flat, the distal face can be oriented at any angle relative to the longitudinal axis of the shaft. While three channels are shown in addition to the needle holder channels, any number of channels can be formed through the elongate shaft, for example by thin wall, tubular sleeves extending longitudinally through the shaft or by voids or spaces defined between the optical fibers as shown. The channels can be parallel to one another or oriented at angles, can be straight or curved, and can be of constant or varying lateral dimension along their length. Furthermore, the channels can be located anywhere within the elongate shaft and can be of the same or different design dependent upon procedural use and space constraints.

The operating channels can have any configuration in transverse cross-section including, but not limited to, elliptical, polygonal and irregular or asymmetrical cross-sectional configurations. Also, all or part of the inner surface of a channel can be electrically insulated to permit passage of electrosurgical instruments therethrough. The valves and couplings shown at the proximal end of each channel are merely exemplary of the types of conventional valves and conventional couplings that can be used. Operating channels may also be defined along the length of the needle driver and the needle catcher of the instrument, if desired. It will also be appreciated that storage spaces or recesses can be defined in the elongate shaft to hold suture needles, lengths of suture material, or other devices.

While the handle assembly shown and described herein is configured to permit essentially one-handed operation of the needle holders, it will be appreciated that other handle configurations can be used including, but not limited to, configurations wherein the handle includes pivoted legs with finger loops, one fixed and one pivoted leg with finger loops, a pistol grip with one or more movable triggers, and/or resilient U-shaped members. It is also possible to mount handle members on both sides of the handle housing so that operation of the needle driver and needle catcher is controlled by separate pairs of handle members as described, for example, in application Ser. No. 08/847,254, the disclosure of which is incorporated herein by reference. Moreover, the handle can have adjustable handle members of variable orientation as shown or handle members which are fixed in a specific orientation relative to the housing. If desired, the housing and at least a portion of the handle can be formed as an integral one-piece unit.

The mechanisms shown for controlling operation of the needle holding members of the needle catcher and the needle driver and movement of the needle catcher and needle driver relative to one another are merely exemplary of the types of mechanisms that can be used to perform these functions. For example, in the case of slidable needle holding members, mechanisms including, but not limited to, controls in the form of push-buttons with wedge-shaped members for engaging flanges carried by each member, resilient U-shaped members with arms connected to each member, and triggers connected to the members via linkages or gears can be used to cause the needle holding members to move relative to one another. In the case of pivoted needle holding members or jaws, mechanisms such as tubular members movable relative to the jaws or linkages connecting one or both of the jaws with a trigger or the like at a proximal end of the instrument can be used to cause the needle holding members or jaws to move relative to one another. The needle holding members can be biased to a particular position, condition or state, such as an open state for receiving a suture needle or a closed state for grasping a suture needle, and can be provided with locking features to permit the user to maintain the members in a desired position.

Moving the needle driver and the needle catcher of the present invention relative to one another can be accomplished in any suitable manner, for example by connecting a knob at the proximal end of each needle holding instrument and sliding the knobs along slots formed in the handle housing or by mounting the needle holding instruments on geared components and moving the gears with a trigger or some other device. The particular length and curvature of the suture needles shown and described herein as well as any angular displacements of the needle driver and catcher shown and described herein are merely exemplary, and it will be appreciated that other needle lengths and angular displacements can be used. It will also be appreciated that the directions and angles of rotation of the needle driver and the needle catcher described and shown herein are for purposes of illustration only and can be reversed and/or altered in magnitude dependent upon procedural use and the preferences of the user.

While the needle holders have been described herein as having a normally bent configuration which can be straightened by retracting the needle holders in a proximal direction relative to a tubular member so as to elastically deform the needle holders, it will be appreciated that the needle holders of the present invention can be moved between contracted and expanded positions using any suitable method including, but not limited to, methods utilizing linkages, gears, cables, movable stiffeners or inserts, shape memory materials, actuators or motors. Dependent upon the angular deflection and length of the bent or angled distal portions of the needle holders, the distal portions may be movable between deployed and parked positions merely by rotation about their respective axes. Also, distal portions of the needle holders need not be straight as shown but can be curved or multiply angled, if desired.

The components of the suturing instrument of the present invention can be made of any suitable, medical grade materials to permit sterilization for reuse or disposal for single patient use. The components can be made of multiple parts of various configurations and materials to reduce cost. The housing and/or handle can have various valves, stop cocks and seals therein to control the flow of fluid and medical devices through the suturing instrument.

The features of the various embodiments described above can be combined in any manner desired dependent upon the operational requirements of the procedure to be performed and the complexity of the suturing instrument. It will also be appreciated that the suturing instrument of the present invention can be used to apply single or multiple stitches in open or endoscopic procedures.

Inasmuch as the present invention is subject to many variations, modifications and changes in detail, it is intended that all subject matter discussed above or shown in the accompanying drawings be interpreted as illustrative only and not be taken in a limiting sense.

What is claimed is:

1. An instrument for suturing anatomical tissue with a suture needle, said suturing instrument comprising
    an elongate shaft having a proximal end and a distal end with a peripheral edge;
    a handle coupled to said proximal end of said shaft;
    a first arm protruding from said distal end of said elongate shaft and having a needle holding portion operable to grasp and release a suture needle; and
    a second arm protruding from said distal end of said elongate shaft and having a needle holding portion operable to grasp and release a suture needle
    said first arm extending laterally outward at an angle from a first longitudinal axis within said elongate shaft to a position where at least a portion of said needle holding portion of said first arm is spaced laterally outward of said peripheral edge of said elongate shaft, said first arm being rotatable about said first longitudinal axis to cause said portion of said first arm to move along a first arcuate path having a center of curvature coaxial with said first longitudinal axis.

2. An instrument as recited in claim 1 wherein said needle holding portion of said first arm is movable between an undeployed position where said needle holding portion of said first arm is spaced laterally inward of said peripheral edge of said elongate shaft and a deployed position where at least a portion of said needle holding portion of said first arm is disposed laterally outward of said peripheral edge.

3. An instrument as recited in claim 2 wherein said first arm is coupled to an elongate proximal member extending at least partly through said shaft in coaxial alignment with said first longitudinal axis.

4. An instrument as recited in claim 3 wherein said first arm is longitudinally movable relative to said elongate shaft between an axially extended position where said first arm bends outwardly in a lateral direction relative to said first longitudinal axis and an axially retracted position where said first arm is drawn inwardly toward said first longitudinal axis.

5. An instrument as recited in claim 4 wherein said needle holding portion of said first arm is proximally spaced from said distal end of said shaft in said retracted position.

6. An instrument as recited in claim 1 wherein a radius of curvature of said first arcuate path is substantially commensurate with a radius of curvature of said suture needle.

7. An instrument as recited in claim 1 wherein said second arm extends laterally outward at an angle from a second longitudinal axis within said elongate shaft to a position where at least a portion of said needle holding portion of said second arm is spaced laterally outward of said peripheral edge of said elongate shaft.

8. An instrument as recited in claim 7 wherein said second arm is rotatable about said second longitudinal axis to cause said needle holding portion of said second arm to move along a second arcuate path having a center of curvature coaxial with said second longitudinal axis.

9. An instrument as recited in claim 8 wherein a radius of curvature of said second arcuate path is substantially commensurate with a radius of curvature of said suture needle.

10. An instrument as recited in claim 8 wherein said first and second arcuate paths intersect one another.

11. An instrument as recited in claim 7 wherein said needle holding portion of said second arm is movable between an undeployed position where said needle holding portion is spaced laterally inward of said peripheral edge of said elongate shaft and a deployed position where at least a portion of said needle holding portion is disposed laterally outward of said peripheral edge.

12. An instrument as recited in claim 11 wherein said second arm is coupled to an elongate proximal member extending at least partly through said shaft in coaxial alignment with said second longitudinal axis.

13. An instrument as recited in claim 12 wherein said second arm is longitudinally movable relative to said elongate shaft between an axially extended position where said first arm bends outwardly in a lateral direction relative to said second axis of rotation and an axially retracted position where said first arm is drawn inwardly toward said second axis of rotation.

14. An instrument as recited in claim 13 wherein said needle holding portion of said second arm is proximally spaced from said distal end of said shaft in said retracted position.

15. An instrument as recited in claim 1 and further comprising an operating channel defined through said elongate shaft to provide access to an operative site from outside of a patient's body when said elongate shaft is inserted into the body to access the operative site within the body.

16. An instrument as recited in claim 1 and further comprising a plurality of operating channels defined through said elongate shaft in laterally spaced relation to provide access to an operative site from outside of a patient's body when said elongate shaft is inserted into the body to access the operative site within the body.

17. An instrument as recited in claim 15 wherein said operating channel extends through said handle to define a longitudinal channel along the length of said instrument, and further comprising a coupling at a proximal end of said channel.

18. An instrument as recited in claim 15 wherein said operating channel defines a longitudinal channel along the length of said instrument, and further comprising a valve disposed along said longitudinal channel to control passage of fluids and instruments therethrough.

19. An instrument as recited in claim 1 wherein an operating channel is defined through said first arm and said elongate shaft to provide access to an operative site from outside patient's body when said elongate shaft is inserted into the body to access the operative site within the body.

20. An instrument as recited in claim 19 wherein said first arm is coupled to an elongate proximal member extending through said elongate shaft and wherein said operating channel terminates distally at an opening adjacent the junction between said elongate proximal member and said first arm.

21. An instrument as recited in claim 1 wherein each of said needle holding portions includes a pair of cooperating needle holding members.

22. An instrument as recited in claim 21 wherein at least one of said needle holding members carries a cutting member.

23. An instrument as recited in claim 21 wherein each pair of needle holding members includes a pair of pivotally opposed jaws.

24. An instrument as recited in claim 23 wherein both of said jaws move relative to one another.

25. An instrument as recited in claim 23 wherein a first of said jaws is fixed and a second of said jaws is movable relative to said first of said jaws.

26. An instrument as recited in claim 23 wherein said first arm and said second arm each include a pair of telescoping inner and outer members axially movable relative to one another, said jaws being mounted at the distal end of said inner telescoping member and being biased apart to an open position such that relative axial movement of the inner and outer telescoping members results in opening and closing of said jaws.

27. An instrument as recited in claim 21 wherein each of said needle holding portions includes a first needle holding member having a distal end in the form of a hook and a second needle holding member having a distal end movable relative to said hook to grasp and release suture needles disposed within said hook.

28. An instrument as recited in claim 27 wherein each of said hooks includes a mouth facing inwardly relative to a central longitudinal axis of said elongate shaft.

29. An instrument as recited in claim 27 wherein each of said hooks includes a mouth facing outwardly relative to a central longitudinal axis of said elongate shaft.

30. An instrument as recited in claim 21 wherein each of said needle holding portions includes a first needle holding member in the form of a tube with a lateral window formed therethrough and a second needle holding member having a distal end movable axially within said tube to grasp and release suture needles disposed within said window.

31. An instrument as recited in claim 30 wherein said windows face inwardly relative to said central longitudinal axis of said elongate shaft.

32. An instrument as recited in claim 30 wherein said windows face outwardly relative to said central longitudinal axis of said elongate shaft.

33. An instrument for suturing anatomical tissue with a suture needle, said instrument comprising an elongate shaft having a proximal end and a distal end with a peripheral edge;

a handle coupled to said distal end of said elongate shaft;

a first needle holder having a proximal portion extending at least part way through said elongate shaft along a first longitudinal axis, a distal arm portion extending laterally outward from said proximal portion at an angle, and a needle holding portion mounted on said distal arm portion and operable to grasp and release a suture needle, said proximal portion of said first needle holder being rotatably mounted within said elongate shaft to move said needle holding portion of said first needle holder along a first arcuate path having a center of curvature coaxial with said first longitudinal axis; and a second needle holder having a proximal portion extending at least part way through said elongate shaft along a second longitudinal axis laterally spaced from said first longitudinal axis, a distal arm portion extending laterally outward from said proximal portion at an angle, and a needle holding portion mounted on said distal arm portion and operable to grasp and release a suture needle, said proximal portion of said second needle holder being rotatably mounted within said elongate shaft to move said needle holding portion of said second needle holder along a second arcuate path having a center of curvature coaxial with said second longitudinal axis.

34. An instrument as recited in claim 33 wherein said second arcuate path has a radius of curvature causing at least a portion of said needle holding portion of said second needle holder to extend outwardly of said peripheral edge of said elongate shaft.

35. An instrument as recited in claim 34 wherein said first and second arcuate paths intersect one another.

36. An instrument as recited in claim 34 wherein said radius of curvature of said first and second arcuate paths is substantially commensurate with the radius of curvature of said suture needle.

37. An instrument as recited in claim 33 wherein said needle holding portions of said first and second needle holders are movable between undeployed positions where said needle holding portions are spaced laterally inward of said peripheral edge of said elongate shaft and deployed positions where at least a portion of each of said needle holding portions is disposed laterally outward of said peripheral edge.

38. An instrument as recited in claim 33 wherein said first and second needle holders are longitudinally movable relative to said elongate shaft between respective axially extended positions where respective distal arm portions of said first and second needle holders bend outwardly in a lateral direction relative to said first and second longitudinal axes, respectively, and respective axially retracted positions where said distal arm portions are drawn inwardly toward said first and second longitudinal axes, respectively.

39. An instrument as recited in claim 38 wherein said needle holding portions of said first and second needle holders are proximally spaced from said distal end of said elongate shaft in said respective retracted positions.

40. A method of suturing anatomical tissue using a length of suture material attached to a suture needle, said method comprising the steps of grasping the suture needle with a needle holding portion of a driver arm protruding distally from the distal end of an elongate shaft, the driver arm extending laterally outward at an angle from a first longitudinal axis within the elongate shaft the needle holding portion;

rotating the driver arm about the first longitudinal axis to drive the suture needle through the anatomical tissue in a first direction along a first arcuate path coaxial with the first longitudinal axis;

receiving the tip of the suture needle in a needle holding portion of a catcher arm protruding distally from the end of the elongate shaft, the catcher arm extending laterally outward at an angle from a second longitudinal axis of the elongate shaft;

grasping the suture needle with the needle catcher arm;

releasing the suture needle from the needle holding portion of the driver arm; and using the needle holding portion of the catcher arm to pull the suture needle through the anatomical tissue in the first direction along a second arcuate path.

41. A method of suturing anatomical tissue as recited in claim 40 and further comprising, prior to said step of rotating the needle driver, the step of causing the needle holding portion of the driver arm to move laterally outward from an undeployed position spaced inwardly of the peripheral edge of the elongate shaft to a deployed position spaced outwardly of the peripheral edge of the elongate shaft.

42. A method of suturing anatomical tissue as recited in claim 40 and further comprising, prior to said step of using the catcher arm, the step of causing the needle holding portion of the catcher arm to move laterally outward from an undeployed position spaced inwardly of the peripheral edge of the elongate shaft to a deployed position spaced outwardly of the peripheral edge of the elongate shaft.

43. A method of suturing anatomical tissue as recited in claim 40 and further comprising, prior to said step of rotating the driver arm, the step of causing the driver arm to move distally relative to the elongate shaft from an axially retracted position within the elongate shaft to an axially extended position protruding from the distal end of the elongate shaft.

44. A method of suturing anatomical tissue as recited in claim 40 and further comprising, prior to said step of using the catcher arm, the step of causing the catcher arm to move distally relative to the elongate shaft from an axially retracted position within the elongate shaft to an axially extended position protruding from the distal end of the elongate shaft.

45. A method of suturing anatomical tissue as recited in claim 40 wherein said step of receiving the suture needle in the needle holding portion of the catcher arm includes the step of rotating the catcher arm about the second longitudinal axis to cause the needle holding portion of the needle catcher to move arcuately in a second direction opposite the first direction.

46. A method of suturing anatomical tissue as recited in claim 40 wherein said step of using the catcher arm includes the step of rotating the catcher arm about the second longitudinal axis to pull the suture needle through the anatomical tissue in the first direction along a second arcuate path coaxial with the second longitudinal axis.

47. A method of suturing anatomical tissue as recited in claim 40 and further comprising, after releasing the suture needle from the needle holding portion of the driver arm, the steps of rotating the driver arm in a second direction opposite the first direction to receive the tip of the suture needle held by the needle holding portion of the catcher arm;

grasping the suture needle with the needle holding portion of the driver arm;

releasing the suture needle from the needle holding portion of the catcher arm; and rotating the driver arm in the first direction to cause the tip of the suture needle to penetrate through the anatomical tissue.

48. A method of suturing anatomical tissue using a length of suture material attached to a suture needle, said method comprising the steps of grasping the suture needle with a needle holding portion of a driver arm protruding distally from the distal end of an elongate shaft, the driver arm extending laterally outward at an angle from a first longitudinal axis within the elongate shaft;

using the driver arm to drive the suture needle through the anatomical tissue in a first direction along a first arcuate path coaxial with the first longitudinal axis;

receiving the tip of the suture needle in a needle holding portion of a catcher arm protruding distally from the distal end of the elongate shaft, the catcher arm extending laterally outward of an angle from a second longitudinal axis within the elongate shaft;

grasping the suture needle with the needle holding portion of the catcher arm;

releasing the suture needle from the needle holding portion of the driver arm; and rotating the catcher arm about the second longitudinal axis to pull the suture needle through the anatomical tissue in the first direction along a second arcuate path.

49. A method of suturing anatomical tissue as recited in claim 48 wherein said step of using the driver arm includes the step of rotating the elongate shaft with the driver arm as a unit about the longitudinal axis of the elongate shaft to drive the suture needle through the anatomical tissue.

50. A method of suturing anatomical tissue as recited in claim 49 wherein said step of receiving the suture needle in the needle holding portion of the catcher arm includes the steps of maintaining the driver arm in a substantially stationary position and rotating the catcher arm along an arcuate path about the longitudinal axis of the elongate shaft in the direction of the needle driver.

51. A method of suturing anatomical tissue as recited in claim 48 and further comprising, prior to said step of using the driver arm, the step of causing the driver arm to move laterally outward from an undeployed position spaced inwardly of the peripheral edge of the elongate shaft to a deployed position spaced outwardly of the peripheral edge of the elongate shaft.

52. A method of suturing anatomical tissue as recited in claim 48 and further comprising, prior to said step of rotating the catcher arm, the step of causing the catcher arm to move laterally outward from an undeployed position spaced inwardly of the peripheral edge of the elongate shaft to a deployed position spaced outwardly of the peripheral edge of the elongate shaft.

53. A method of suturing anatomical tissue as recited in claim 48 and further comprising, prior to said step of using the driver arm, the step of causing the driver arm to move distally relative to the elongate shaft from an axially retracted position within the elongate shaft to an axially extended position protruding from the distal end of the elongate shaft.

54. A method of suturing anatomical tissue as recited in claim 48 and further comprising, prior to said step of rotating the arm, the step of causing the catcher arm to move distally relative to the elongate shaft from an axially retracted position within the elongate shaft to an axially extended position protruding from the distal end of the elongate shaft.

55. A method of suturing anatomical tissue as recited in claim 48 wherein said step of receiving the suture needle in the needle holding portion of the catcher arm includes the step of rotating the catcher arm about the second longitudinal axis of the elongate shaft to cause the needle holding portion of the catcher arm to move arcuately in a second direction opposite the first direction.

56. A method of suturing anatomical tissue as recited in claim 48 and further comprising, after releasing the suture needle from the needle holding portion of the driver arm, the steps of rotating the driver arm in a second direction opposite the first direction to receive the tip of the suture needle held by the needle catcher in the needle holding portion of the driver arm;

grasping the suture needle with the needle holding portion of the driver arm;

releasing the suture needle from the needle holding portion of the catcher arm; and rotating the driver arm in the first direction to cause the tip of the suture needle to penetrate through the anatomical tissue.

57. An instrument as recited in claim 33 wherein said first arcuate path has a radius of curvature causing at least a portion of said needle holding portion of said second needle holder to extend outwardly of said peripheral edge of said elongate shaft.

58. A method of suturing anatomical tissue as recited in claim 40 wherein the first arcuate path and the second arcuate path pass outside of a peripheral edge of the elongate shaft.

59. A method of suturing anatomical tissue as recited in claim 45 wherein said steps of rotating the driver arm and rotating the catcher arm are conducted simultaneously.

60. A method of suturing anatomical tissue as recited in claim 48 wherein the first arcuate path and the second arcuate path pass outside of a peripheral edge of the elongate shaft.

* * * * *